(12) United States Patent
Chandra et al.

(10) Patent No.: US 7,865,534 B2
(45) Date of Patent: Jan. 4, 2011

(54) SYSTEM, METHOD AND APPARATUS FOR ASSEMBLING AND MINING LIFE SCIENCE DATA

(75) Inventors: D. Navin Chandra, Framingham, MA (US); Fatima Chandra, legal representative, Framingham, MA (US); Dexter R. Pratt, Reading, MA (US); Eric K. Neumann, Lexington, MA (US); Keith O. Elliston, Sudbury, MA (US); Justin Sun, Norwood, MA (US); Ted M. Slater, Saline, MI (US)

(73) Assignee: Genstruct, Inc., Cambridge, MA (US)

( * ) Notice: Subject to any disclaimer, the term of this patent is extended or adjusted under 35 U.S.C. 154(b) by 406 days.

(21) Appl. No.: 10/644,582

(22) Filed: Aug. 20, 2003

(65) Prior Publication Data

US 2005/0038608 A1 Feb. 17, 2005

Related U.S. Application Data

(60) Provisional application No. 60/414,637, filed on Sep. 30, 2002.

(51) Int. Cl.
G06F 17/30 (2006.01)

(52) U.S. Cl. .................... 707/805; 707/798; 702/19; 702/20; 706/45

(58) Field of Classification Search ......... 707/100–102, 707/798, 803, 805; 702/19–20, 27; 706/45
See application file for complete search history.

(56) References Cited

U.S. PATENT DOCUMENTS 4,935,877 A 6/1990 Koza

| 5,136,686 A | 8/1992 | Koza |
| 5,148,513 A | 9/1992 | Koza et al. |
| 5,343,554 A | 8/1994 | Koza et al. |
| 5,390,282 A | 2/1995 | Koza et al. |
| 5,742,738 A | 4/1998 | Koza et al. |

(Continued)

FOREIGN PATENT DOCUMENTS

EP 1248231 10/2002

(Continued)

OTHER PUBLICATIONS

Goldberg, David E., "Genetic and Evolutionary Algorithms Come of Age," Communications of the ACM, vol. 37, No. 3, Mar. 1994, pp. 113-119.

(Continued)

*Primary Examiner*—Khanh B Pham
(74) *Attorney, Agent, or Firm*—David H. Judson

(57) ABSTRACT

Method and system for managing and evaluating life science data. Life Science data is placed in a knowledge base, that may be used for a variety of analysis tasks. Creating a knowledge base from the life science data involves generating two or more nodes indicative of life science data, assigning to one or more pairs of nodes a representation descriptor that corresponds to a relationship between the nodes, and assembling the nodes and the relationship descriptor into a database, such that at least one of the nodes is joined to another node by a representation descriptor. In some embodiments, the representation descriptor includes a case frame that describes the relationships between elements of life science data.

25 Claims, 17 Drawing Sheets

U.S. PATENT DOCUMENTS

| | | | |
|---|---|---|---|
| 5,867,397 | A | 2/1999 | Koza et al. |
| 5,914,891 | A | 6/1999 | McAdams et al. |
| 6,058,385 | A | 5/2000 | Koza et al. |
| 6,360,191 | B1 | 3/2002 | Koza et al. |
| 6,424,959 | B1 | 7/2002 | Bennett, III et al. |
| 6,532,453 | B1 | 3/2003 | Koza et al. |
| 6,564,194 | B1 | 5/2003 | Koza et al. |
| 6,594,587 | B2 | 7/2003 | Askenazi |
| 6,665,669 | B2 | 12/2003 | Han et al. |
| 6,741,986 | B2 | 5/2004 | Cho et al. |
| 6,772,160 | B2 | 8/2004 | Cho et al. |
| 2001/0016822 | A1 | 8/2001 | Bessette |
| 2001/0047353 | A1 | 11/2001 | Talib et al. |
| 2002/0002559 | A1 | 1/2002 | Busa |
| 2002/0049782 | A1 | 4/2002 | Herzenberg et al. |
| 2002/0087275 | A1* | 7/2002 | Kim et al. .................. 702/19 |
| 2002/0123847 | A1* | 9/2002 | Askenazi .................. 702/20 |
| 2002/0198858 | A1* | 12/2002 | Stanley et al. ............. 706/50 |
| 2003/0074516 | A1 | 4/2003 | Cho et al. |

FOREIGN PATENT DOCUMENTS

| | | |
|---|---|---|
| WO | WO 02/11048 A2 | 2/2002 |
| WO | WO 02/093409 | 11/2002 |
| WO | WO 03/067504 A2 | 8/2003 |
| WO | WO 03/082214 | 10/2003 |

OTHER PUBLICATIONS van Helden, Jacques, etal., "Representing and Analysing Molecular and Cellular Function Using the Computer," Biol. Chem., vol. 381, pp. 921-935, Sep.-Oct. 2000.

Uetz, Peter, et al., "Visualization and Integration of Protein-Protein Interactions," in Golemis E (ed.) *Protein-Protein Interactions—A Molecular Cloning Manual*, Cold Spring Harbor Laboratory Press (available at: http://itgmv1.fzk.de/www/itg/uetz/publications/Visualization.pdf), 2002.

International Search Report for International Application No. PCT/US/2005/00202 mailed from the International Searching Authority on Nov. 24, 2005.

Written Opinion of the International Searching Authority for International Application No. PCT/US/2005/00202 mailed from the International Searching Authority on Nov. 24, 2005.

International Search Report for PCT/US03/36857, mailed Mar. 9, 2005.

International Preliminary Report on Patentability for PCT/US2004/039159 dated May 29, 2006.

Written Opinion of the International Searching Authority for PCT/US2004/039159 dated May 29, 2006.

International Search Report for International Application No. PCT/US/2004/039159 mailed from the International Searching Authority on Aug. 31, 2005.

Written Opinion of the International Searching Authority for International Application No. PCT/US/2004/039159 mailed from the International Searching Authority on Aug. 31, 2005.

Kanehisa, Minoru et al, "The KEGG Databases at GenomeNet," Nucleic Acids Research, vol. 30, No. 1, pp. 42-46 (2002).

European Search Report for Application No. PCT/US03/30653 dated Sep. 6, 2007 (3 pages).

Center for Development of Advanced Computing, "Workshop on Genetic Algorithms in Bioinformatics," http://www.cdacindia.com/html/ecents/bioinfo/genetic/genidx.asp, pp. 1-6 (printed Oct. 22, 2002).

Jansen, Ronald, "A Bayesian Networks Approach for Predicting Protein-Protein Interactiojns from Genomic Data," Science, vol. 302, pp. 449-453 (Oct. 17, 2003).

Karp, Peter D., "The EcoCyc Database," pp. 1-6 (Jan. 25, 2002).

Karp, Peter D., "Integrated Access to Metabolic and Genomic Data," pp. 1-32 (Apr. 1, 1996).

Karp, Peter D., "The MetaCyc Database," pp. 1-7 (Jan. 25, 2002).

Karp, Peter D., "Pathway Databases: A Case Study in Computational Symbolic Theories," Science, vol. 293, pp. 2040-2044 (Sep. 14, 2001).

Karp, Peter D., "The Pathway Tools Software," Bioinformatics, vol. 18 Suppl. 1 2002, pp. S1-S8 (2002).

Koza, John R., "Reverse Engineering and Automatic Synthesis of Metabolic Pathways From Observed Data Using Genetic Programming," pp. 1-53 (2000).

Koza, John R., "Reverse Engineering and Automatic Synthesis of Metabolic Pathways From Observed Data Using Genetic Programming," Symposium on Computational Discovery of Communicatable Knowledge, pp. 1-63 (Mar. 25, 2001).

Koza, John R., "Reverse Engineering and Automatic Synthesis of Metabolic Pathways From Observed Data Using Genetic Programming," Biomedical Informatics, pp. 1-12, Aug. 2000.

Rindfleisch, Thomas C., "Extracting Molecular Binding Relationships from Biomedical Text," pp. 188-195, 2000.

Stevens, Robert "Building a Reason-able Bioinformatics Ontology Using OIL," Department of Computer Science, University of Manchester, pp. 1-11, Aug. 2001.

Yen, John, "A Hybrid Approach to Modeling Metabolic Systems Using Genetic Algorithm and Siomplex Method," pp. 1-42, Feb. 1995.

Yen, John, "Using Fuzzy Logic and a Hybrid Genetic Algorithm for Metabolic Modeling," pp. 1-6, 1996.

International Search Report for PCT/US2003/030653, mailed Feb. 3, 2004.

* cited by examiner

Genstruct Biopathway Knowledge Assembler
The Knowledge Assembly Company

HISTORY

Browser: search for an enzyme or molecule

Keyword Search name ▾ | *pyruvate* — 852

Select from 19 terms ▾ — Filtered 241 terms.

Select from 19 terms — ns only

5:pyruvate oxidation
1:pyruvate transport
3:Phosphoenolpyruvate
2:Pyruvate Dehydrogenase Complex Mm
5:glycerol biosynthesis from pyruvate
1:acetyl-CoA biosynthesis from pyruvate
2:Catalytic Activity of pyruvate dehydrogenase complex
4:pyruvate dehydrogenase complex Hs phosphorylated at ?
2:Pyruvate Dehydrogenase Complex Mm phosphorylated at S
2:pyruvate dehydrogenase complex Rn phosphorylated at ?
21:Catalytic Activity of pyruvate dehydrogenase complex Hs
6:Catalytic Activity of Pyruvate Dehydrogenase Complex Mm
5:Catalytic Activity of pyruvate dehydrogenase complex Rn
3:[pyruvate dehydrogenase (lipoamide)] phosphatase activity
2:Activation of Catalytic Activity of pyruvate dehydrogenase complex Hs by serum glucose
1:Pyruvate Dehydrogenase Complex Mm --> Pyruvate Dehydrogenase Complex Mm phosphorylated at S
1:Activation of pyruvate oxidation by Kinase Activity of AMP-activated protein kinase complex Hs
35:Pyruvate : Propanoic acid, 2-oxo-, ion(1-)
53:Pyruvate oxid... : Thioctic acid

— 854

Back to top

*FIG. 9*

Browser: search for an enzyme or molecule

| name | ⌄ | *pyruvate* | | | | Keyword Search |

21:Catalytic Activity of pyruvate dehydrogenase complex Hs  ⌄  - Filtered 241 terms.

Filter by Organism | Filter by Object Type | Options
☑ All Species | ☑ All Objects | ☑ Objects with Causal Connections only
☐ Human | ☐ Protein | ☑ Show counts of Causal Connection
☐ Mouse | ☐ Gene Expression | ☑ Hide Homologene Edits
☐ Rat | | ☑ Hide Removed Assertions

[Search]

900 ↙

---

Term ID 869917: Catalytic Activity of pyruvate dehydrogenase complex Hs

Assertions

| Relationship | Associated Information | Attribution | Source |

Summary (2)   Homologous (0)   Activation (11)   Inhibition (10)   Binding/Complex (0)   Miscellaneous (1)
                              Upstream Downstream   Upstream Downstream Summary Assertions (2)                                                        Back to Top catalyzedBy    pyruvate dehydrogenase complex Hs    15169745    basic/complexes.bel instanceOf     EnzymaticReaction template           15169745    core/core_ontology.bel

»Select type of path find »Select sources/targets »Verify sources/targets

Source Reference Type:
BEL Term

Sources:
estradiol

Separate sources by a new line or the pipe ("|") character.

Target Reference Type:
BEL Term — 1202

Targets:
mapk1

Separate targets by a new line or the pipe ("|") character.

Previous    Next

1200

Hypothesis Scores | Tab 2 ✕ | ＋

Zoom: 0.25 ——●———— 8

Nodes | Edges

| Source | Relationship | Target |
|---|---|---|
| Estradiol-17beta | -> | MAPK1 P@? |
| Estradiol-17beta | -> | MAPK1 P@Y1 |
| Estradiol-17beta | -> | kaof(MEK Fam |
| MAPK1 P@? | -@- | MAPK1 |
| MAPK1 P@T185 | -@- | MAPK1 |
| MAPK1 P@T187 | -@- | MAPK1 |
| kaof(MEK Family Hs) | => | MAPK1 P@T1 |

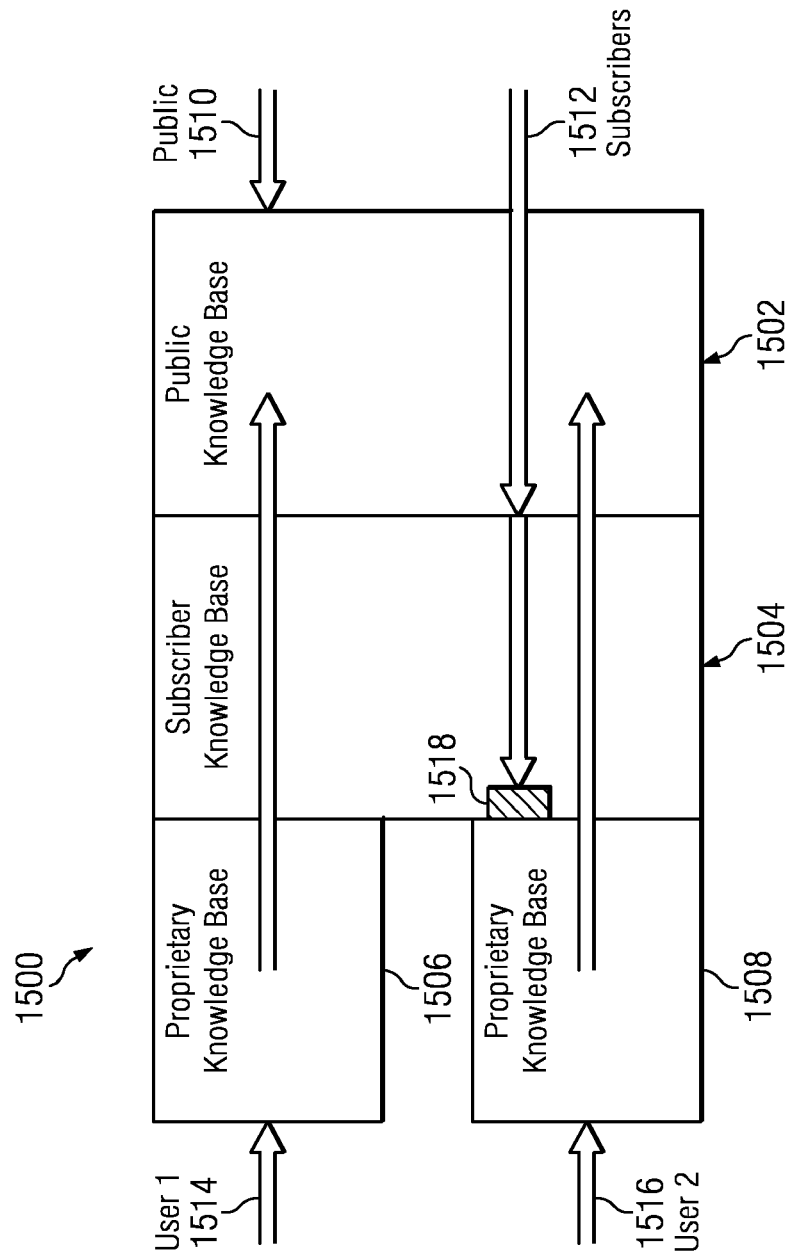

SYSTEM, METHOD AND APPARATUS FOR ASSEMBLING AND MINING LIFE SCIENCE DATA

RELATED APPLICATIONS

This application claims the benefit of U.S. provisional application No. 60/414,637, entitled "System, Method and Apparatus for Assembling and Mining Life Science Data," filed Sep. 30, 2002, the disclosure of which is incorporated by reference herein.

TECHNICAL FIELD

The invention relates to the field of data management and evaluation. In particular, the invention relates to the processing and organization of life science data.

BACKGROUND

Life science information is information relevant to the understanding of the structures, behaviors, operations, maladies, and processes of plant and animal life, and includes the nature of the work that generated it, the identity of the people who generated it, and assessments of its significance and context within the encyclopedic, ever growing life science knowledge-base of mankind.

Traditional methods of discerning and understanding the meaning of life science information are breaking down due to the large amount of material that must be absorbed and combined. New and old information are presented and stored in public, publicly accessible, proprietary, and private databases of different structures, printed or electronic journals, scholarly theses, patents, medical records, master files, books, clinical trial files, government data compilations, etc. These information sources exist in different formats, different languages, different data structures, conflicting vocabulary and ontology, and often are presented based on inconsistent and competing theories. The accessibility of these data for study and knowledge mining ranges from completely inaccessible trade secret data, to data available only by subscription, to current data generated by a colleague but not yet communicated, to obscure observations in a language foreign to the reader, to free public information a few clicks away. To form an effective understanding of a biological system, a life science researcher must synthesize information from many of these sources.

Understanding biological systems is made more difficult by the interdisciplinary nature of the life sciences. Forming an understanding of a system may require in-depth knowledge of genetics, cell biology, biochemistry, medicine, and many other fields. The literature in these fields often are addressed to specialists who do not frequently communicate outside their specialties: the protein chemist may not talk to and does not read the literature of the epidemiologist; the synthetic chemist may relate poorly to the molecular biologist.

Understanding a biological system may require that information of many different types be combined. Life science information may include material on basic chemistry, proteins, cells, tissues, and effects on organisms or population— all of which may be interrelated. These interrelations may be complex, poorly understood, or hidden.

Knowledge useful in the development of human therapies and the like is gained by inspired individuals seeking out and combining disparate data and then reasoning from it. Currently, progress is made as scientists locate and access diverse data sources, pose questions, seek other data in an attempt to refine or eliminate a hypothesis or make a connection, and devise and conduct new experiments. The scientist then publishes or otherwise records his new data, exposing it for review, criticism, and use by others. As knowledge increases, it become apparent that no person can possibly access, much less assimilate, all the available data in any field. Furthermore, the amount of data generated in the life sciences is increasing dramatically, with no end in sight. Those seeking new insights and new knowledge are presented with the ever more difficult task of connecting the right data from mountains of information gleaned from vastly different sources. Thus, to the extent our current system of generating and recording life science data has been developed to permit knowledge mining, it is clearly far from optimal, and significant new efficiencies should be available.

What is needed is a way to assemble and store vast amounts of life science information, and to make that information available in a manner that enhances understanding of the interrelationships within the information. It would be desirable to provide a system and methods that allow researchers to assemble life science data and mine information in a comprehensive manner that facilitates the understanding and revelation of the possibly hidden interactions of a biological system.

SUMMARY OF THE INVENTION

The present invention proposes and enables a new paradigm for the recordation, organization, access, and application of life science data. The method and program enables establishment and ongoing development of a systematic, ontologically consistent, flexible, optimally accessible, evolving, organic, life science knowledge base. A knowledge base according to embodiments of the invention represents and stores biological information of many different types, from many different sources. The knowledge base represents and stores information on many types of relationships within the life science information.

A knowledge base according to embodiments of the invention places life science information into a form that exposes the relationships within the information, facilitates efficient knowledge mining, and makes the information more readily comprehensible and available. Such a life science knowledge base can be used in a manner similar to a library, providing a way for researchers, physicians, students, drug discovery companies, and many others to access life science information in a way that enhances the understanding of the information.

The knowledge base may be continuously built up and refined, to provide a complete electronic paradigm for harmonizing the vast array of life science information. It is envisioned that a knowledge base according to an embodiment of the invention could eventually incorporate the entirety of human life science knowledge from its finest detail to its global effect.

In one aspect, the invention provides a method of assembling a life science knowledge base by generating two or more nodes indicative of life science data using a life science taxonomy, assigning to one or more pairs of nodes a representation descriptor that corresponds to a relationship between a pair of nodes, and assembling two or more nodes and one or more representation descriptors into an electronic database, such that at least one of the nodes is joined to another node by a representation descriptor. In some embodiments, the representations descriptors are themselves nodes, and can be joined to other nodes by representation descriptors.

In some embodiments, the method includes the step of receiving life science data, and generating the two or more nodes is based at least in part on the received life science data. In certain such embodiments, receiving life science data includes collecting life science data using a software agent. In some embodiments, receiving life science data further includes receiving one or more of metadata and context data.

In some embodiments, the life science data includes information representative of a molecule, biological structure, physiological condition, trait, or phenotype. In some embodiments, the life science data includes a descriptor of the condition, location, amount, or substructure of a molecule, biological structure, physiological condition, trait, or phenotype.

In some embodiments the step of generating two or more nodes includes reformatting at least a portion of the life science data.

In some embodiments, one or more of the representation descriptors include a case frame.

Some embodiments include a step of providing an ontology for use with the representation descriptors, and the step of assigning a representation descriptor to one or more pairs of nodes is based on the ontology.

Some embodiments include the step of segregating the electronic database into two or more sectors, such that access may be restricted to one or more selected sectors.

In another aspect, the invention provides an article of manufacture having a computer-readable program carrier with computer-readable instructions embodied thereon for performing the methods described above.

In another aspect, the invention provides a system for assembling a life science knowledge base. The system includes a data collector configured to receive life science data and to generate nodes based on the life science data. The system also includes a relationship generator configured to assign a relationship descriptor to a pair of nodes, the representation descriptor corresponding to a relationship between a pair of nodes. The system further includes a knowledge assembler configured to assemble two or more nodes and one or more representation descriptors assigned to one or more pairs of the two or more nodes into an electronic database such that each of the two or more nodes are joined to another node by a representation descriptor.

In some embodiments, the system also includes a graphical user interface configured to permit a user to query the electronic database at least on the relationship between at least two nodes.

In some embodiments, the system includes a data input interface configured to permit a user to submit life science data to the data collector. In some such embodiments, the data input interface is further configured to permit a user to assign a representation descriptor to a pair of nodes in the electronic database. In some embodiments, the data input interface may be configured to permit a user to create, replace, update, and delete nodes and representation descriptors.

In some embodiments, the system also includes an access manager configured to restrict access of a user to one or more portions of the electronic database.

In some embodiments, the system further includes a software agent in electronic communication with the data collector, wherein the software agent is configured to collect life science data.

In some embodiments, the life science data includes information representative of a molecule, biological structure, physiological condition, trait, or phenotype. In some embodiments, the life science data includes a descriptor of the condition, location, amount, or substructure of a molecule, biological structure, physiological condition trait or phenotype.

Is some embodiments, the system also includes a library of machine-readable representation descriptors in electronic communication with the relationship generator. The relationship descriptors in some embodiments correspond to an epistemological relationship between a pair of nodes. In some embodiments, one or more of the representation descriptors includes a case frame.

In another aspect, the invention provides a computer program product that includes an electronic database storing a plurality of case statements, each case statement comprising an object identifier, a relationship connector, and a biological object identifier, wherein the relationship connector is based on a life science ontology.

In some embodiments, a set of the case statements define a biological function. In some such embodiments, the biological function involves a chemical reaction. In some embodiments, the biological function involves transport. In some embodiments, the biological function involves digestion of a biomolecule.

In some embodiments, the biological object identifier identifies a biomolecule. In some embodiments, the biological object identifier identifies a biological function.

In some embodiments, the relationship connector represents an identity relationship. In some embodiments, the relationship connector represents a product relationship. In some embodiments, the relationship connector represents a substrate relationship. In some embodiments, the relationship connector represents an enzymatic relationship.

In some embodiments, the product also includes a graphical user interface configured to permit a user to query the database at least on the relationship between biological object identifiers.

In some embodiments, the product further includes a data input interface configured to permit a user to create case statements.

In another aspect, the invention provides an article of manufacture where the functionality of one or more of the methods of the invention are embedded on a computer-readable program means, such as, but not limited to, a floppy disk, a hard disk, an optical disk, a magnetic tape, a PROM, an EPROM, CD-ROM, or DVD-ROM.

In a further aspect, the invention provides a method of representing life science knowledge using case frames. The case frames include a first object identifier, a relationship connector, and a second object identifier. The relationship connector is based on a life science ontology. These case frames may be used to represent a wide variety of life science information.

The foregoing and other features and advantages of the invention, as well as the invention itself, will be more fully understood from the description, drawings, and claims which follow.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 9 shows an example of a search screen according to an embodiment of the invention;

FIG. 10 shows an example of a screen in which a relationship type is selected and information is added to a case frame according to an embodiment of the invention;

FIG. 12 shows a screen illustrating use of a knowledge base to find paths according to an embodiment of the invention;

FIG. 15 is a block diagram showing access restrictions on proprietary portions of a knowledge base according to an embodiment of the invention.

DESCRIPTION

In accordance with the invention, biological and other Life Sciences knowledge can be represented and manipulated in a computer environment so that the knowledge can be stored and shared. Such Life Sciences knowledge can be reasoned upon by algorithms that are designed to derive new knowledge and make novel conclusions relevant to furthering the understanding of biological systems and underlying mechanisms in Life Sciences. Providing such a knowledge base permits harmonization of numerous types of life science information from numerous sources.

Figure 1:
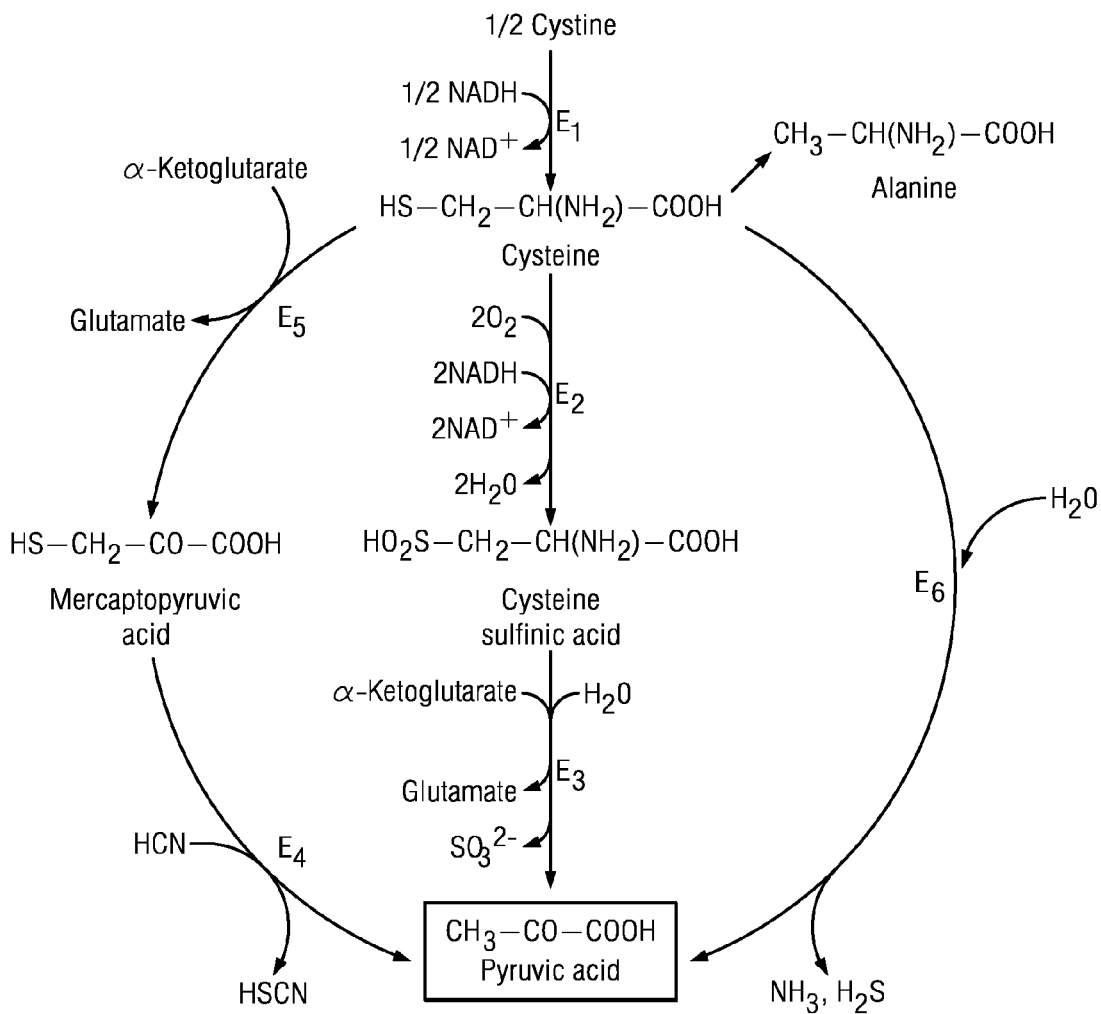
FIG. 1 is a diagrammatic overview of a biological system illustrating the complexity and some of the relationships between the components of the system.

FIG. 1 is a diagram showing an example biological system. As can be seen, the system includes various entities, including molecular entities, and numerous relationships between them. To reason about the system shown in FIG. 1 as a whole requires knowledge of the entire system. A change or problem at any point in the system could have effects throughout the entire system.

Figure 2:
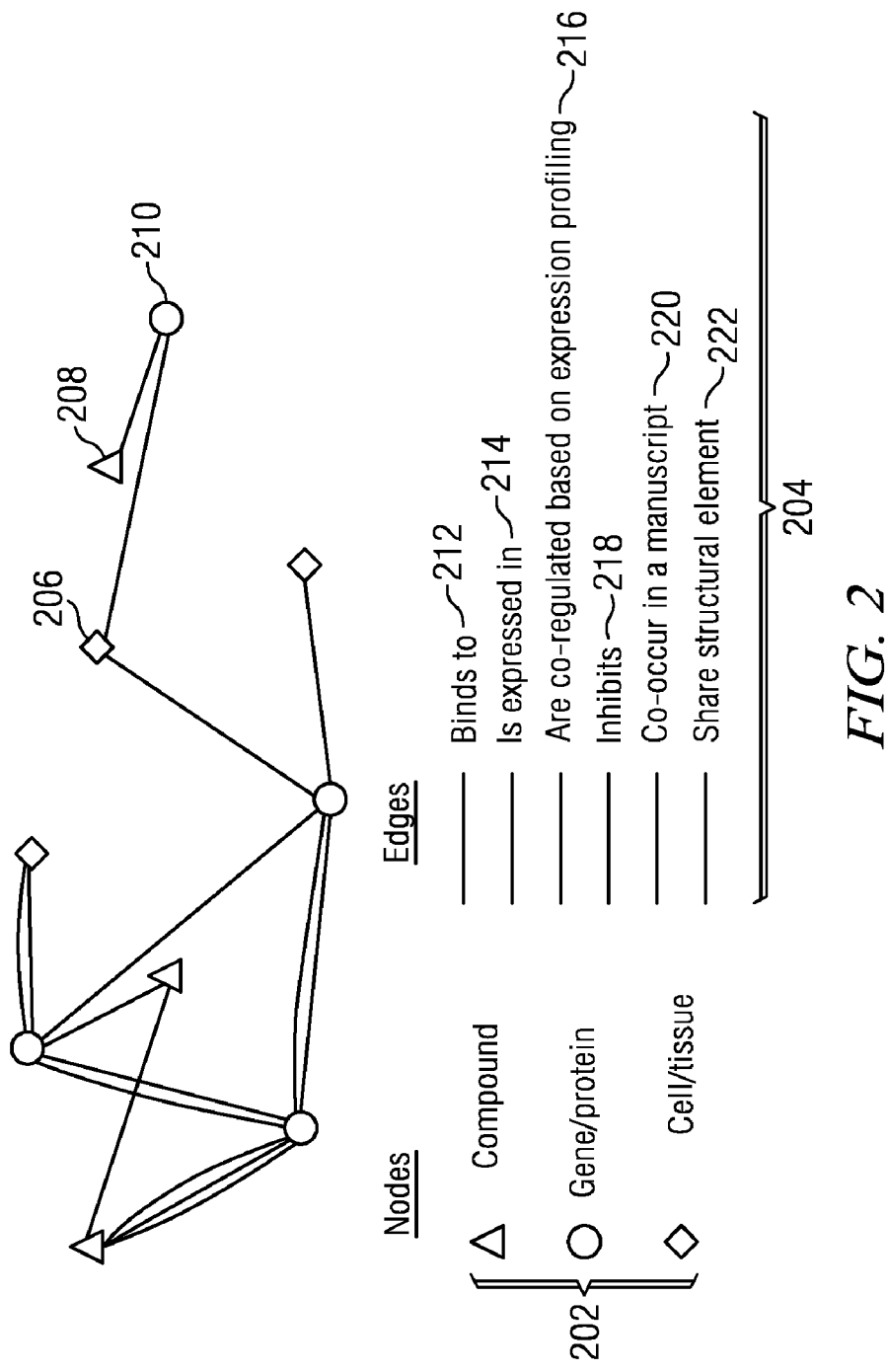
FIG. 2 is a schematic illustration of an embodiment of a graph structure according to the present invention for representing life science knowledge.

In accordance with one embodiment of the invention, a system such as that shown in FIG. 1 may be represented as a graph, such as is shown in FIG. 2. The graph shown in FIG. 2 includes nodes 202 and edges 204. The nodes 202 represent entities within a biological system, such as compounds, genes, proteins, cells, and tissues. The edges 204 represent relationships between the nodes 202.

In the example shown in FIG. 2, various types of nodes are represented by different shapes. For example, a diamond-shaped node, such as the node 206, represents a cell or tissue. A triangle-shaped node, such as the node 208, represents a compound. A circle-shaped node, such as the node 210, represents a gene or protein. Thus, the life science data represented by the nodes may be based on a life science taxonomy, in which each particular entity to be represented by a node in the graph is classified according to its type.

The edges in the graph represent various relations between the nodes, as shown in FIG. 2. For example, edges may represent a "binds to" relation 212, an "is expressed in" relation 214, an "are co-regulated based on expression profiling" relation 216, an "inhibits" relation 218, a "co-occur in a manuscript" relation 220, or a "share structural element" relation 222. These types of relationships between the nodes may be referred to as "representation descriptors." Generally, a representation descriptor describes a relationship between a pair of nodes. These relationships may be referred to as epistemological relationships between nodes, since they represent knowledge about the relation of one entity to another.

In accordance with an embodiment of the invention, the nodes in the graph may also represent relationships between nodes. Thus, it is possible to represent relationships between relationships, or relationships between a relationship and another type of life science entity represented in the graph. For example a relationship between two nodes that represent chemicals may represent a reaction. This reaction may be a node in a relationship between the reaction and a chemical that inhibits the reaction.

In accordance with an embodiment of the invention, the entities and relationships (i.e., the nodes and edges) that make up a graph, such as the graph shown in FIG. 2, may be stored as a web of interrelated nodes in a knowledge base. Various algorithms may be applied to such graphs to provide automated reasoning capabilities, for knowledge assembly and mining.

Figure 3A:
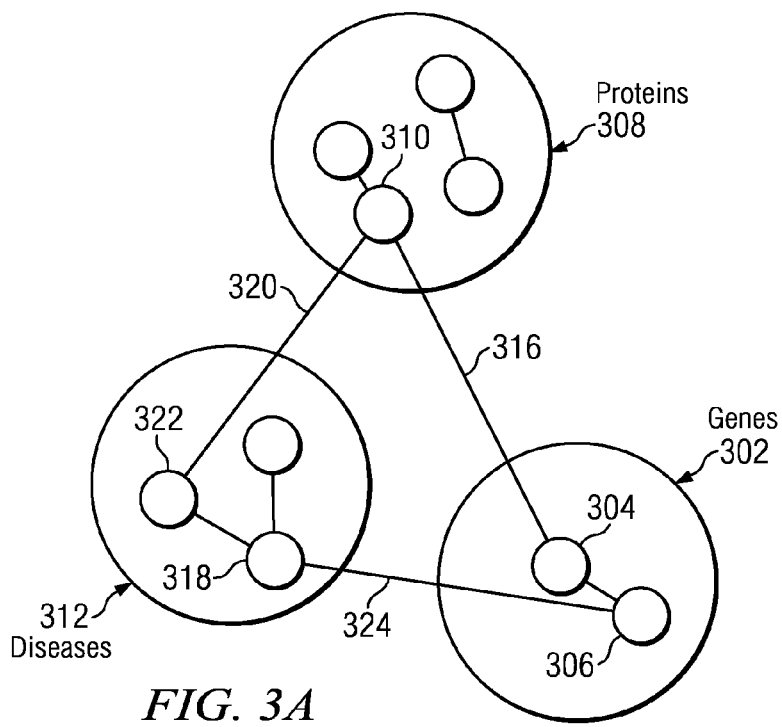
FIGS. 3A-B are schematic illustrations of an embodiment of a knowledge base according to the present invention, in which multiple datasets are interconnected by relationships to form the knowledge base.

The knowledge represented within the life science knowledge base may be of various different types, drawn from various different sources. For example, FIG. 3A shows three separate sets of data, representing different types of life sciences information. A dataset 302 is a genomic database, including information on genes, and relations between them. For example, a node 304 may represent an oncogene, while a node 306 represents a gene that inhibits the gene represented by the node 304.

A dataset 308 represents proteins, and relations between them. Thus, a node 310 in dataset 308 may represent a particular protein. Similarly, a dataset 312 represents diseases and their interrelations, and nodes in dataset 308 may represent various disease states.

Each of the datasets 302, 308, and 312 could be a knowledge base in its own right, as each contains a representation of knowledge on a particular topic of relevance to the life sciences. However, as shown in FIG. 3A, a greater knowledge base may be formed by creating connections between the datasets 302, 308, and 312, based on knowledge of the relations between genes, proteins, and diseases.

For example, relations, such as a relation 316, may represent the knowledge that a particular gene codes for or produces a particular protein. A lack or abundance of a particular protein or set of proteins may be associated with particular diseases. For example, a relation 320 may indicate that an abundance of the protein represented by the node 310 in the protein dataset 308 causes the disease (e.g., cancer) represented by the node 322 in the disease dataset 312.

Relations can be created between any members of any datasets. For example, a gene represented by the node 306 in the gene dataset 302 may be directly linked to a disease state represented by a node 318 in the disease dataset 312 by a relation 324.

Figure 3B:
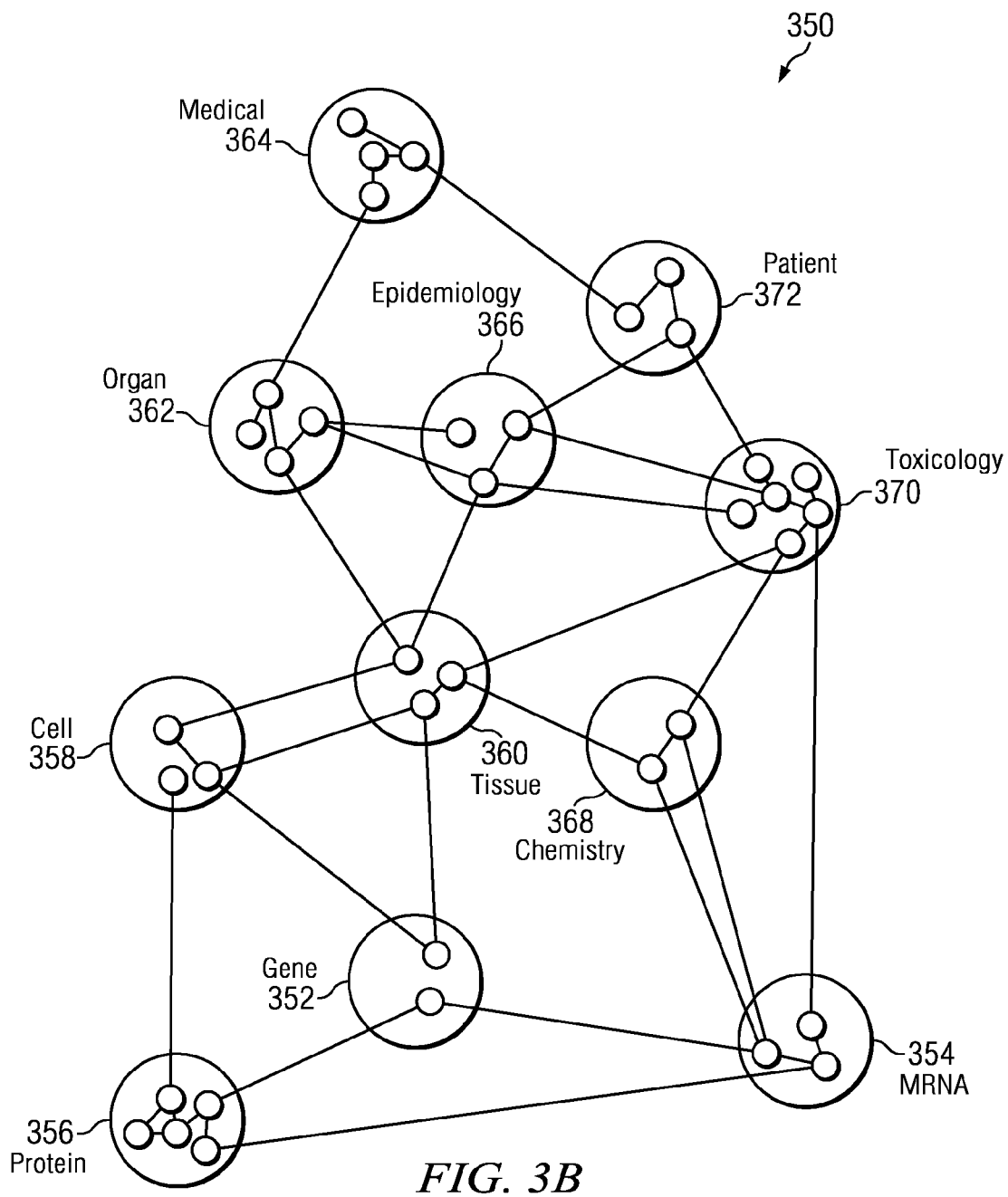

As can be seen in FIG. 3B, there are many different types of life science data that can be combined in a knowledge base. Knowledge base 350 includes a web of relations between nodes representing knowledge in a gene dataset 352, an MRNA dataset 354, a protein dataset 356, a cell dataset 358, a tissue dataset 360, an organ dataset 362, a medical dataset 364, an epidemiology dataset 366, a chemistry dataset 368, a toxicology dataset 370, and a patient dataset 372. All of these datasets contain nodes that represent life science information, and the nodes in each of the datasets may be related to nodes in the same dataset, or in other datasets.

Knowledge base 350 contains a wide variety of life science information, across many fields. The information in knowledge base 350 ranges from genetic information, in gene dataset 352, to medical information, in medical dataset 364, to information on individual patients in patient dataset 372, and on entire populations, in epidemiology dataset 366.

In addition to the various datasets that are shown in FIG. 3B, there may be many other datasets, or types of life science information that may be included in a knowledge base in accordance with an embodiment of the invention. For example, a knowledge base could further include medical record data, structure/activity relationship data, information on infectious pathology, information on clinical trials, and any other type of life science information. By interconnecting information of numerous types and from a variety of fields, as shown in FIG. 3B, a knowledge base according to an embodiment of the invention may harmonize and combine many types of life science information, and provide researchers with the ability to find and understand the many relationships between life science information.

In one embodiment, the nodes and representation descriptors that represent life sciences information are built up in a knowledge base using case frames. A case frame provides a representational formalism for life sciences knowledge and data. As will be more fully described below, each case frame corresponse to a specific concept in the life sciences and consists of two or more nodes indicative of life science data, with one or more relationship descriptors between and among the nodes.

These case frames may be made available in a library, from which they may be selected and instantiated to form a knowledge base. The case frames in the library can be viewed as templates, because specific information has not been specified for each node and relationship. During instantiation, these "blanks": are filled in, to form an instance of the case frame in a knowledge base. As case frames are instantiated, those that share common nodes and/or relationships may be clustered to form a network of connected case frames.

Alternatively, nodes and relationships can be built up and represented in a relational database, an object-oriented environment, a logic-based environment, or in other database or programming paradigms.

Figure 4A:
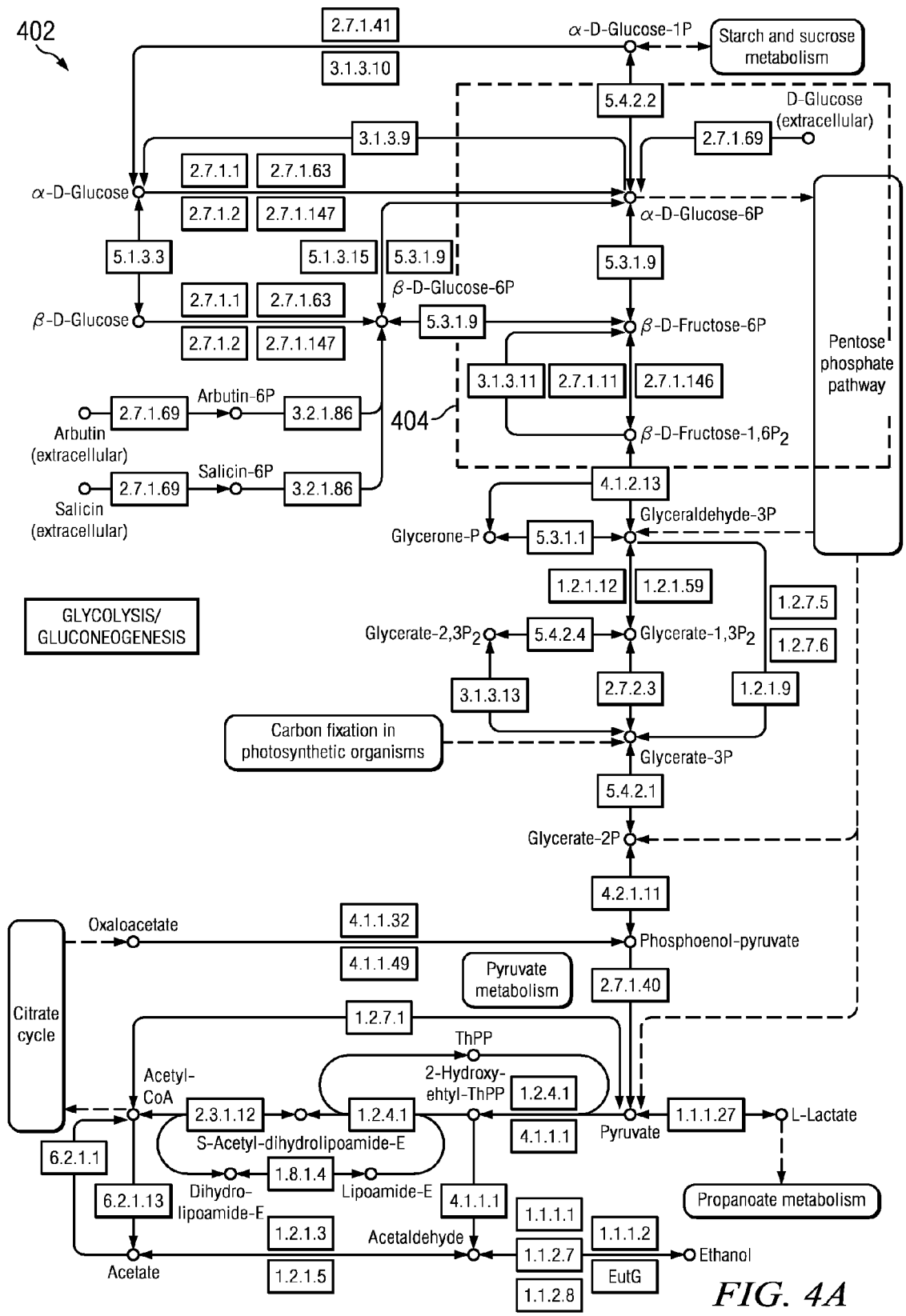
FIG. 4 is a schematic illustration of an embodiment of generating nodes and assigning representation descriptors according to the present invention showing using case frames.
Figure 4B:
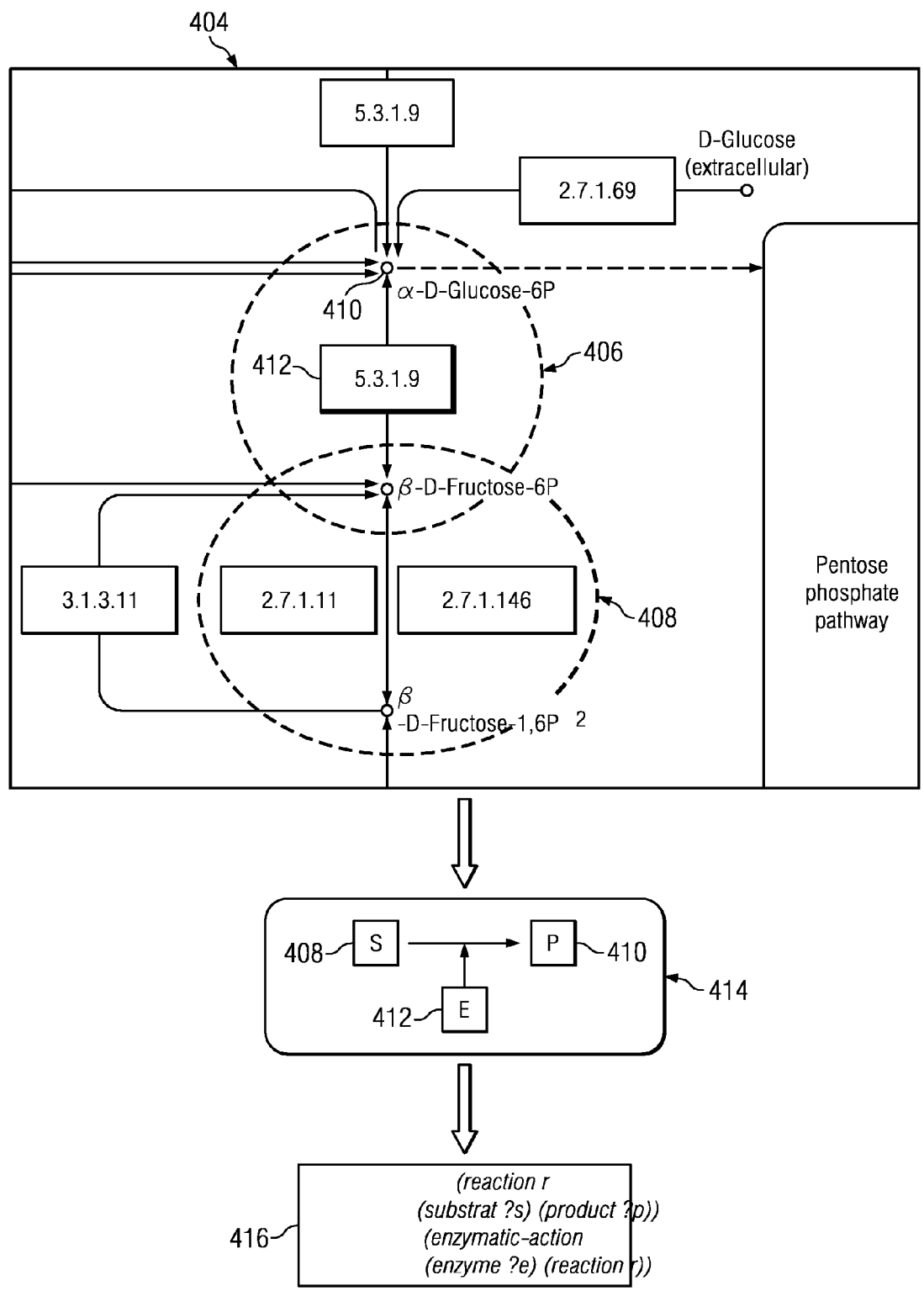

Referring to FIG. 4, construction of case frames from life sciences information is illustrated. In this example, a reaction 406, shown in a portion 404 of a metabolic pathway 402 is to be added to the knowledge base. Reaction 406 is an enzymatic reaction in which a substrate 408 (in this case, β-D-Fructose-6P) is transformed into a product 410 (in this case, α-D-Glucose-6P) through the action of an enzyme 412.

A case frame 414 is used to represent the information. In this instance, the case frame 414 represents the substrate 408 being transformed to the product 410 through a reaction involving enzyme 412. The information may then be transformed into a computer-readable representation 416, for storage in a knowledge base, and manipulation by automated reasoning algorithms.

Knowledge from the metabolic pathway 402 may be placed in a knowledge base using numerous case frames, such as case frame 406.

Figure 5:
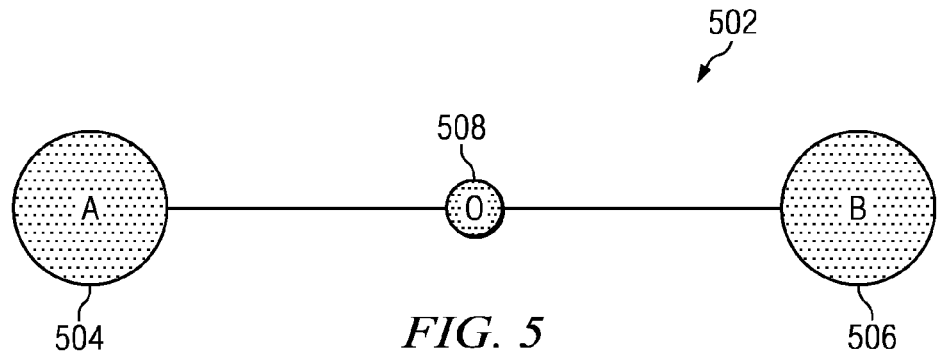
FIG. 5 is a schematic illustration of a case frame according to an embodiment of the present invention.

Referring to FIG. 5, a general example of a case frame for representing particular life sciences knowledge is described. The case frame 502 of FIG. 5 includes an entry A 504 and an entry B 506. The entries A 504 and B 506 are related by a relation R 508. Each of the entries A 504 and B 506 represent objects of relevance in the life sciences, such as proteins, enzymes, genes, cells, tissues, compounds, molecules, or other life science-related objects.

Each of the entries A 504, B 506, and the relation R 508 may be associated with various attributes, and may be connected to entries or relations (not shown). Using a collection of case frames, such as case frame 502, large networks of life science knowledge may be built.

Figure 6:
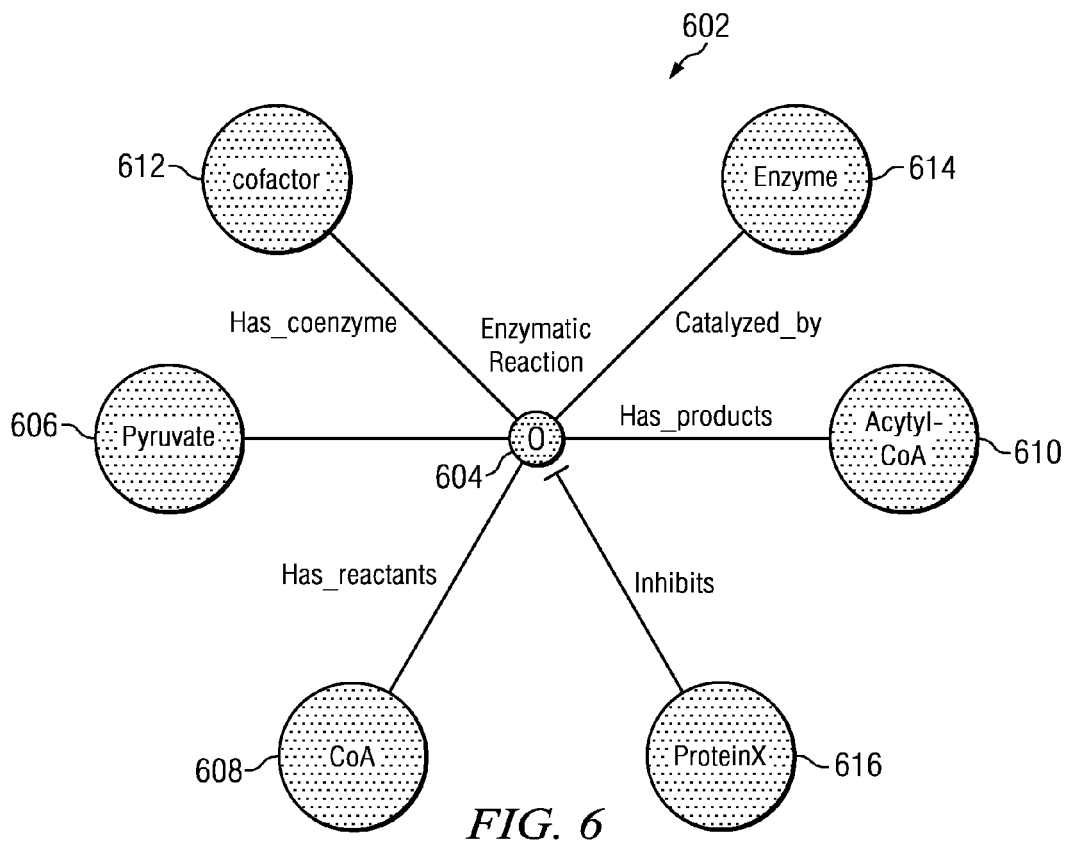
FIG. 6 is a schematic illustration of a case frame representing an enzymatic reaction according to an embodiment of the invention.

FIG. 6 shows an instance of a case frame 602, which is somewhat more complex than the case frame 502 of FIG. 5. The central relation R 604 of the case frame 602 represents an enzymatic reaction. The enzymatic reaction shown in the case frame 602 has reactants Pyruvate 606 and CoA 608, and produces Acetyl-CoA 610. The enzymatic reaction has a coenzyme cofactor 612, is catalyzed by an enzyme 614, and is inhibited by a protein X 616 (the arrow for inhibition is shown in FIG. 6 as being different than the other arrows).

The case frame 602 can be converted into a pseudocode form. For example, known languages, such as XML or Java may be used to represent a case frame, such as the case frame 602. Although the syntax of the pseudocode may vary, the types of objects, attributes, and relations will be the same. An example of pseudocode representing the case frame 602 is:

Create Relation Called R1
R1 has reaction CoA
R1 has reactant Pyruvate
R1 is catalyzed_by Enzyme
R1 has product Acetyl-CoA
R1 is—a enzymatic reaction
R1 has_coenzyme cofactor
Protein X inhibits R1

Generic forms of case frames may be produced. For example, a generic or empty case frame for an enzymatic reaction could be represented as:

Create Relation Called (R1)
R1 has reactant _____
R1 has reactant _____
. . . (repeat for all substrates)
R1 is catalyzed_by _____
R1 is catalyzed_by _____
. . . (repeat for all catalysts)
R1 has product _____
R1 has product _____
. . . (repeat for all products)
R1 is—a enzymatic reaction
R1 has_coenzyme _____
R1 has_coenzyme _____
. . . (repeat for all cofactors)
R1 occurs in tissue _____ (repeat for all tissues)
R1 occurs in compartment $_{13}$ _____ (repeat for all sub-cellular compartments)
R1 occurs in species _____ (repeat for all species)
R1 is inhibited by _____ (repeat for all)

This empty or generic case frame may be used to represent any enzymatic reaction in any known organism or tissue. This type of representation of a case frame permits any aspect of a reaction to be represented. Additionally, other aspects may be added, such as energy levels, species data and other supporting data as it becomes available.

A library of such empty or generic case frames can be built to represent substantially all of the known atomic concepts in life sciences. By creating such a library of empty case frames, complex concepts in life sciences can be represented by filling in the blanks in the appropriate set of case frames from the library of generic or empty case frames.

The empty or generic case frame shown above represents an enzymatic reaction. This same case frame can be generalized to show various reactions, such as a protein binding or an activation of transcription. The statement in the example shown above that says that relation R1 is a enzymatic reaction can be replaced by one of many terms such as:

R1 is—a protein_binding relation
R1 is—a activation realtion
R1 is—a inhibition relation
R1 is—a auto-phosphyrylation relation
R1 is—a comentioned-in-the-literature relation
R1 is—a has-related-patent relation Generally, case frames can be built using terms that represent objects, classes of objects, events, or classes of events. Some of these terms represent relationships between terms, such as one term being a subset of another. In one embodiment, case frames are based on terms that specify individuals (i.e., individual objects or events), classes (i.e., classes of individuals), relationships (i.e., relationships between other terms), and metaclasses (i.e., classes of classes).

Examples of classes include types of life science objects, such as chemicals, organisms, reactions, processes, etc., as well as types of objects that are used for bookkeeping or other uses, such as databases and documents. Similarly, relations may include life science relations, such as "catalyzed by", "activates", and "inhibits", as well as other types of relations, such as "keggMapID", which is a relation used to specify that an object is referenced with a specific ID in the KEGG database, or "subset of", which specifies that one term is a subset of another. An examples of a metaclass is "species", in which instances are classes of organism which are designated as species in a standard classification scheme, and "basic term type."

Figure 7A:
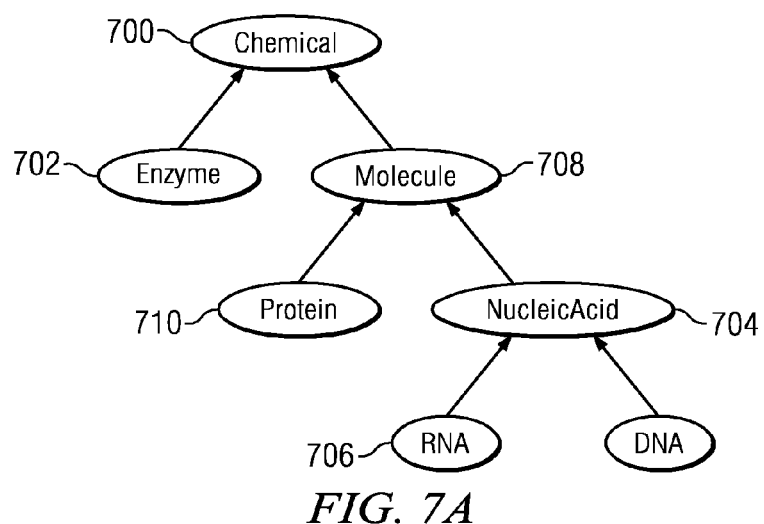
FIGS. 7A-G are schematic illustrations showing various case frames and relations between them according to illustrative embodiments of the invention.

FIG. 7A shows relationships between classes of case frames that are used in one embodiment of the present invention for representing chemicals. The arrows in the diagram represent a "subset of" relationship. Thus, for example, an enzyme class 702 is a subset of a chemical class 700, and an RNA class 706 is a subset of a Nucleic Acid class 704.

The structure of the subset relations shown in FIG. 7A is useful for facilitating reasoning about the various classes of chemical. In this example, a "chemical" is defined as any chemical entity, from macromolecules to hydrogen ions. A "molecule" (i.e., molecule class 708 is defined as a chemical in which the atoms are primarily covalently linked. The enzyme class 702 is a subset of the chemical class 700, rather than a protein class 710 or the molecule class 708, since enzymatic reactions may be catalyzed by ribozymes or molecular complexes.

Case frames are also used for representing interactions. In one embodiment, such interactions are a class (which is a subset of a "physical process" class) of events where chemicals and/or cellular components affect each other. Examples of such interactions include a reaction class, a binding class, a gene expression class, and increase class, a decrease class, a translocation class, an activation class, and an inhibition class.

Figure 7B:
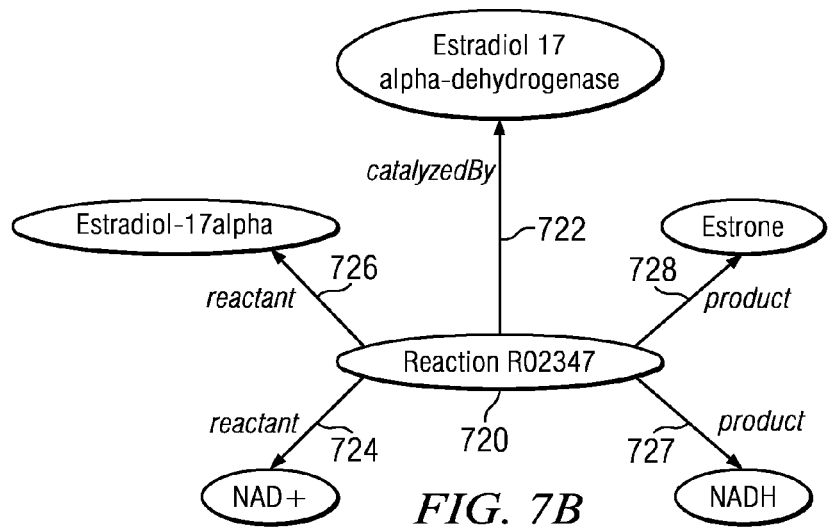

FIG. 7B shows an example instance of an enzymatic reaction, which is a subset of a reaction. As can be seen, an enzymatic reaction 720 is characterized by assertions using various relationships. An "X catalyzedBy Y" relationship 722 represents a relationship in which reactions of type X (in this instance, Reaction R02347) are catalyzed by enzyme molecules of type Y (in this instance, Estradiol 17 alpha-dehydrogenase). similarly, an "X reactant Y" relationship, such as relationships 724 and 726, represents that reactions of type X consume chemicals of type Y. An "X product Y" relationship, such as relationships 727 and 728, which represents that reactions of type X produce chemicals of type Y.

In addition to the relations shown in FIG. 7B, a case frame representing an enzymatic reaction my include other relationships. For example, an "X cofactor Y" relationship (not shown) may be used to represent that the chemical with the name Y binds to the enzyme as a necessary cofactor in reactions of type X. Note that this implies that an "X reactant Y" relationship. An "X effector Y" relationship (not shown) may be used to represent that interactions of type X are effected by chemicals whose name is Y. An "X inhibitingChemical Y" relationship (not shown) represents that interactions of type X are inhibited by chemicals whose name is Y.

In one embodiment, some classes of EnzymaticReaction correspond exactly to a particular EC number. These classes are instances of the metaclass "ECClass," and represent classes of reaction that cross species boundaries, and have been grouped by EC on the basis of function.

Case frames are used in some embodiments of the invention to represent genes, proteins, and RNA, and relationships between them. For example, structural protein relationships may be represented by an "X hasProteinBindingDomain Y" that indicates that proteins of type X have a protein domain of type Y. Functional protein relationships may also be represented.

Figure 7C:
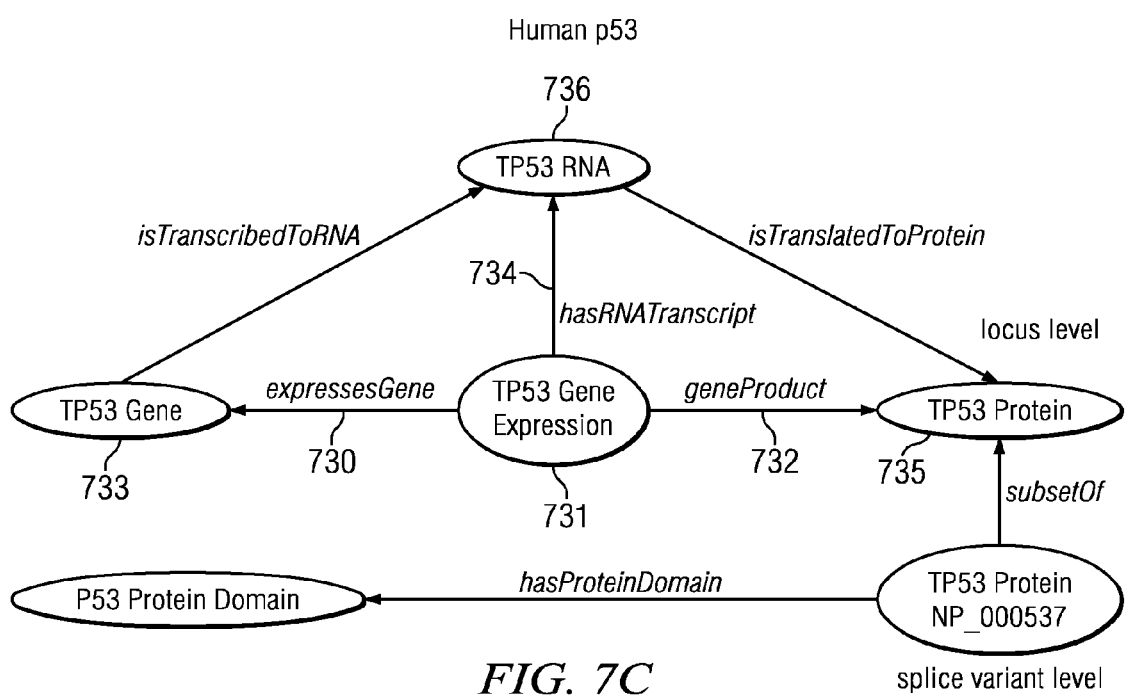

FIG. 7C shows an example case frame for representing gene expression. In the example shown in FIG. 7C, gene expression for the human p53 gene is shown. An "expressesGene" relationship 730 indicates that the TP53 gene expression 731 expresses the TP53 gene 733. a "geneProduct" relationship 732 indicates that the TP53 protein 735 is produced by the TP53 gene expression 731. A "hasRNATranscript" relationship 734 indicates that TP53 RNA 736 is the RNA transcript of the TP53 gene expression 731. The TP53 gene 733 has an "is TranscribedToRNA" relationship with the TP53 RNA 736, which has an "is TranslatedToProtein" relationship with the TP53 protein 735.

Generally, a GeneExpression is characterized by assertions using the following relationships:

| | |
|---|---|
| X expressesGene Y | X is a type of GeneExpression that expresses Gene Y |
| X geneProduct Y | a Chemical Y is produced by a GeneExpression of type X |
| X upregulatedBy Y | GeneExpressions of type X are upregulated by things of type Y |
| X downregulatedBy Y | GeneExpressions of type X are downregulated by things of type Y |
| X regulatedBy Y | GeneExpressions of type X are affected by things of type Y |

Additionally, genes, proteins, and RNA may be further characterized by the following relationships in a case frame:

| | |
|---|---|
| X translatesRNA Y | RNA of type Y is translated as part of GeneExpression of type X |
| X homologousGene Y | Gene X is homologous to gene Y |
| X isTranscribedToRNA Y | There exists gene expression such that gene X is transcribed to RNA Y |
| X isTranslatedToProtein Y | There exists gene expression such that RNA X is translated to Protein Y |
| X transcriptionModulationSite Y | Y is a binding site that affects the transcription of gene X |
| X cytogeneticPosition Y | Y is the location of gene X within its chromosome |
| X onChromosomeNumber Y | The species-specific number of the chromosome on which a gene is located |
| X syntheticallyLethalWith Y | Either gene X or gene Y is sufficient for the organism to survive, but at least one is required |

Figure 7D:
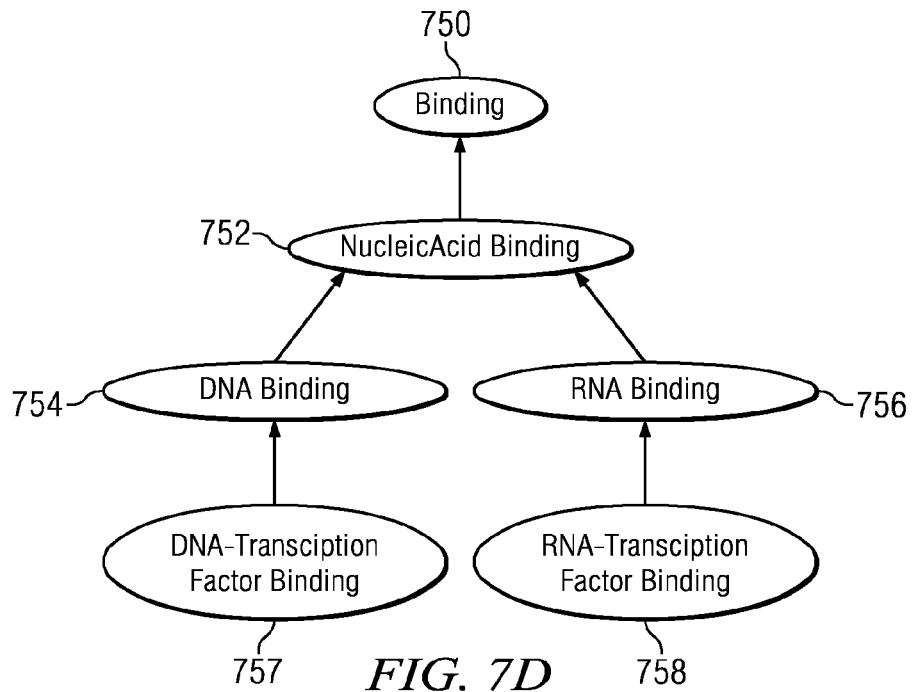

Referring to FIG. 7D, the relationship between various case frames that are used in some embodiments of the invention to represent binding is shown. A "NucleicAcid Binding" class 752 is a subset of a general "binding" class 750. A "DNA Binding" class 754 and an "RNA Binding" class 756 are subsets of the "NucleicAcid Binding" class 752. A "DNA-Transcription Factor Binding" class 757 is a subset of the "DNA Binding" class 754, and an "RNA-Transcription Factor Binding" class 758 is a subset of the "RNA Binding" class 756. In some embodiments, certain of the classes that define bindings correspond to GO terms.

Additional classes related to binding include an "Unbinding" class (not shown), and a "MolecularComplex" class (not shown). A "MolecularComplex" is a class of chemical characterized by assertions that use an "X complexComponent Y" relationship, which represents that complexes of type X include molecules or molecular complexes of type Y.

A binding interaction is a class of process that is characterized by assertions using the following relationships:

| | |
|---|---|
| X bindingInput Y | Bindings of type X involve molecules or molecular complexes of type Y |
| X bindingOutput Z | Bindings of type X produce complexes of type Z |

Figure 7G:
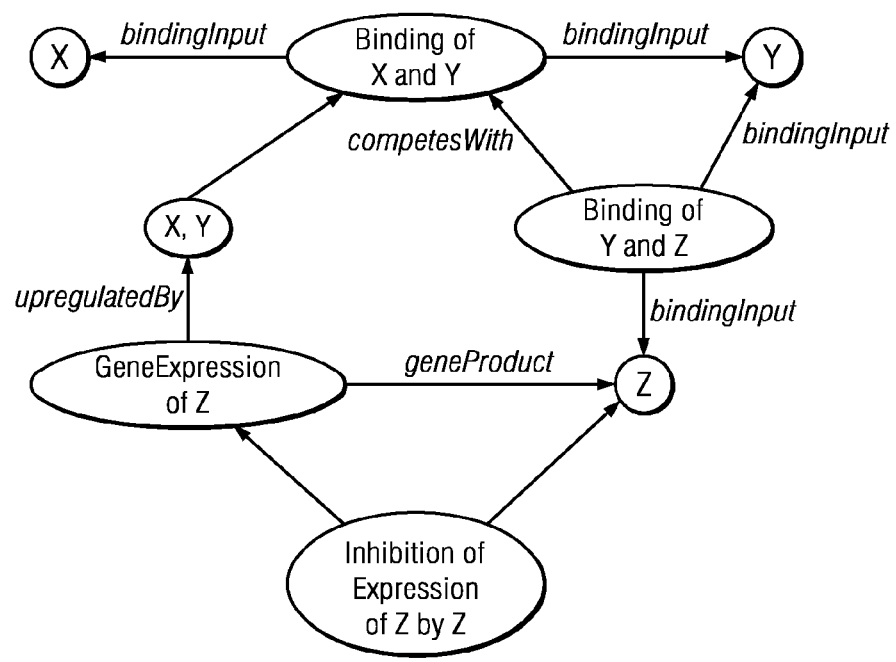
Figure 7E:
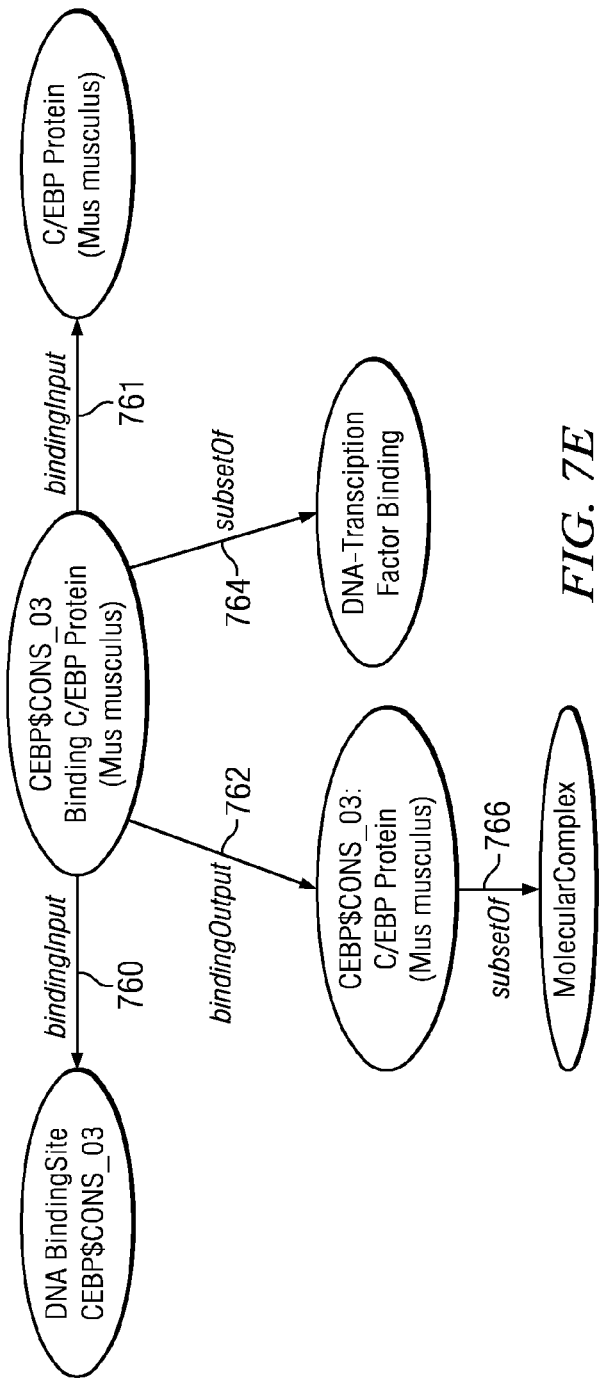

An example of the use of such relations is shown in FIG. 7E, in which "bindingInput" relationships 760 and 761, and a "bindingOutput" relationship 762 are used to specify the inputs and output of a binding process. Other relationships, such as "subsetOf" relationships 764 and 766 are used to specify that the binding process is a subset of a DNA-transcription factor binding (relationship 764), and that the output of the binding is a subset of a molecular complex (relationship 766).

In some embodiments, molecular complexes are represented by a class of chemical characterized by assertions using a "complexComponent" relationship. The "X complexComponent Y" relationship indicates that complexes of type X include molecules or molecular complexes of type Y. In some embodiments, the "complexComponent" relationship may include a numeric literal that specifies the number of molecules or molexular complexes of a given class. Thus, a "X complexComponent Y N" relationship specifies that complexes of type X include N molecules or molecular complexes of type Y. This type of relationships can be used to represent homodimers, homotrimers, homotetramers, etc.

In some embodiments, case frames are used to represent modifications of polymers. For linear polymers, such case frames are characterized by a relationships or assertions that indicate the type and position of the modification. Included in such modifications of polymers are case frames for representing post-translational modifications of proteins. This may include case frames that represent phosphorylation, acetylation, peptide-bond cleavage, glycosylayion, lipidation (including fatty-acylation and prenylation), methylation, metallation, cross-linking, hydroxylation, sulfation ADP-ribosylation, and covalent attachment of prosthetic groups such as flavin and heme. This may be accomplished by relationships specific to each type of modification, such as the following:

| | |
|---|---|
| X phosphorylatedAt N | Proteins of type X are phosphorylated at position N |
| X acetylatedAt N | Polymers of type X are acetylated at position N |
| X ribosylatedAt N | Polymers of type X are ribosylated at position N |
| X cleavedAt N | Polymers of type X are the remainder after cleavage at position N |
| X glycosylatedAt N | Polymers of type X are glycosylated at position N |
| X methylatedAt N | Polymers of type X are methylated at position N |
| X lipidatedAt N | Polymers of type X are lipidated at position N |
| X fattyAcylatedAt N | Polymers of type X are fatty-acylated at position N |
| X metallationAt N | Polymers of type X are metallated at position N |
| X hydroxylatedAt N | Polymers of type X are hydroxylated at position N |
| X sulfatedAt N | Polymers of type X are sulfated at position N |

Figure 7F:
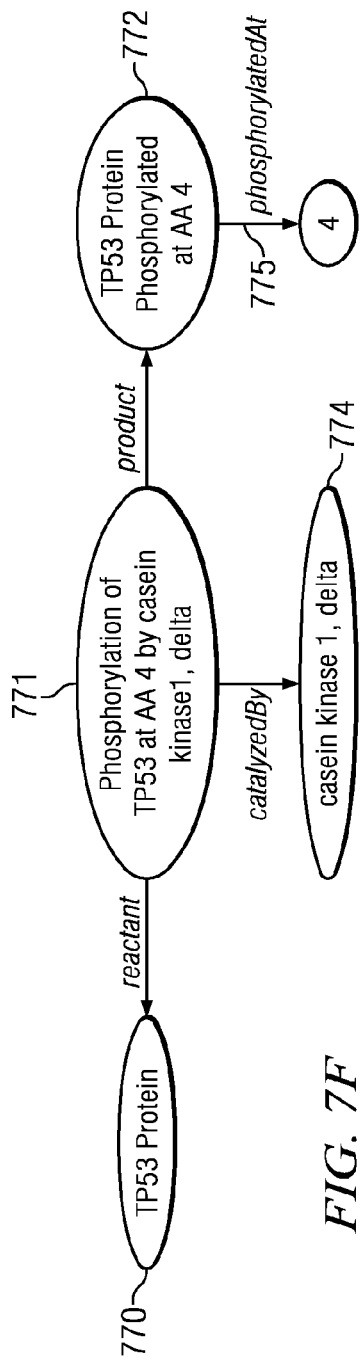

FIG. 7F shows an example of a phosphorylation reaction 771, which may be represented as an enzymatic reaction in which the reactant 770 is a protein, and the product 772 is a modified subclass of protein. The kinase 774 that performs the phosphorylation is the catalyst for the reaction. The "phosphorylatedAt" relationship 775 is used to indicate the position at which the product 772 is phosphorylated. Other post-translational modifications may be handled in the same manner as phosphorylations.

In some embodiments, if there are multiple kinases that may produce the same phosphorylation, each reaction is represented as a separate class of process, all of which share a common product. This feature of the representation permits the product to be used in other relationships, such as inhibations and activations, rather than starting a separate relationship for each reaction that produces the product.

The removal of modifications, such as deacetylations, may be represented as negated assertions on the products. In such cases, the modified product class is the subset of polymer that is explicitly known to not be modified at a given position.

In some embodiments, case frames are used to represent causal relationships, such as activation and inhibition, also referred to as "increase" and "decrease" or "upregulated" or "downregulated". Activation and inhibition are subsets of modulation, which is a subset of a process class. Generally, activation and inhibition connect a cause—the "inhibitor" or "activator"—with a process that is affected by the activation or inhibition. They can also connect a cause with a biological entity, indicating that the cause modulates the abundance of the entity. Note that since activation and inhibition are a subset of process, it is possible to represent an activation or inhibition being activated or inhibited.

Direct activation and indirect Inhibition are subsets of activation and inhibition, respectively. They indicate that instances of a class directly affect instances of a process. Regular activation and inhibition do not necessarily imply such an immediate causal relationship. The cause of a regular activation or inhibition may be many steps removed, or may not be known.

In some embodiments, Activations are connected to other classes by the relationships "activates" and "activator". The "X activates Y" relationship indicates that things of type Y are activated by activations of type X. The "X activator Y" relationship indicates that activations of type X are caused by things of type Y.

Similarly, inhibitions are connected to other classes by the relationships "inhibits" and "inhibitor". The "X inhibits Y" relationship indicates that things of type Y are inhibited in inhibitions of type X. The "X inhibitor Y" relationship indicates that inhibitions of type X are caused by things of type Y.

In some embodiments, case frames are used to represent competition between processes. An "X competeswith Y" relationship indicates that processes of type X compete with processes of type Y. While such competition can frequently be inferred, the "competeswith" relationship permits it to be explicitly stated as a case frame.

In some embodiments, case frames are used to represent the requirements of processes. An "X requires Y" relationship indicates that processes of type X require the presence of objects or processes of type Y. Note that although a "requires" relationship indicates a dependency, the nature of the dependency is not known. The "requires" relationship does not imply that increases in the required objects or processes will increase the process, but does imply that decreases in the required objects or processes will decrease the process.

In some embodiments, case frames are used to represent translocations. Such translocations are processes that represent change in location for classes of objects. The relationships for a translocation indicate the type of object and type of locations.

Translocations may be directional translocations, in which the objects are transported from one type of location to another type, but not the reverse. There are also translocations that connect two locations, indicating that the objects may move in both directions. This is a common case where molecules able to pass a barrier, such as a membrane, are in equilibrium across the barrier, such that a net flow of molecules is due to their creation, destruction, or other removal on one side of the barrier.

The relationships that characterize a translocatin are listed in the following table:

| | |
|---|---|
| X tranlocates Y | Things of type Y change location in translocations of type X. |
| X translocatedFrom Y | In translocations of type X, the objects that change location are initially at locations of type Y. |
| X translocatedTo Y | In translocations of type X, the objects that change location move to locations of type Y. |
| X translocatedBy Y | In translocations of type X the translocation is accomplished or affected by the biological entity or process Y |

The following table provides a list of case frames, including classes, metaclasses, and relationships, that are used to represent life-sciences information related to molecular biology:

| | |
|---|---|
| C1 subsetOf C2 | C1 subsetOf C2: C2 is a class which is a superset of the class C1 |
| X instanceOf C | X instanceOf C: X is a member of class C |
| MetaClass; TaxonomicClass | Instances are Classes which form the standard classification scheme for organisms |
| MetaClass: Species | "Instances are Classes of Organism which are designated as Species in the standard classification scheme |
| MetaClass: OrganismStrain | Instances are Classes of Organism which are genetically distinguished and which are more specific than Species |
| MetaClass: OrganismAnamorph | Instances are Classes of Organism which distinct morphological forms of a species, such as an asexual form of a Fungal species. Should be a subset of a species and has the same genome as the species. |
| Class: PhysicalObject | Physically existing individual object |
| Class: Chemical | Any chemical entity, from macromolecules to hydrogen ions. |
| Class: Molecule | Instances are chemicals in which the atoms are primarily covalently linked |
| Class: Polymer Extent | A linear polymeric molecule or a sub-region of a linear polymeric molecule. The sequence of units of the extent may or may not be known |
| Class: NucleicAcid Extent | NucleicAcid molecule or a sub-region of a NucleicAcid molecule, such as a binding site or gene. The sequence of the extent may or may not be known |
| Class: NucleicAcid | |
| Class: Artificial NucleicAcid Sequence | An artificially created NucleicAcid molecule with a specified sequence |
| Class: DNA Extent | DNA molecule or a sub-region of a DNA molecule, such as a binding site or gene. The sequence of the extent may or may not be known |
| Class: DNA | DNA molecule or a subsequence of a DNA molecule - i.e. a binding site is also DNA |

| | |
|---|---|
| Class: RNA Extent | RNA molecule or a sub-region of a RNA molecule, such as a binding site or gene. The sequence of the extent may or may not be known |
| Class: RNA | RNA molecule or a subsequence of an RNA molecule |
| Class: NucleicAcid BindingSite | Sequence of NucleicAcid identified by its ability to participate in a binding interaction with a molecule or molecular complex |
| Class: DNA BindingSite | Sequence of DNA identified by its ability to participate in a binding interaction with a molecule or molecular complex |
| Class: RNA BindingSite | Sequence of RNA identified by its ability to participate in a binding interaction with a molecule or molecular complex |
| Class: DNA PromoterSite | DNA BindingSite which acts as a promoter for the Gene when it is bound |
| Class; DNA EnhancerSite | DNA BindingSite which acts as an enhancer for the Gene when it is bound |
| Class: SmallMolecule | Molecules typically smaller than proteins and other macromolecules" |
| Class: Protein Extent | Protein molecule or a sub-region of a Protein molecule, such as a Protein Domain. The sequence of the extent may or may not be known |
| Class: Protein | A polypeptide sequence |
| Class: ProteinDomain | A region of a protein. Typically a region which has biologically significant binding activity |
| Class: Enzyme | A Chemical which catalyzes specific reactions. |
| Class: Gene | A portion of DNA (or in some cases RNA) which can be expressed into gene products by an Organism |
| Class: Process | Events or Processes" |
| Class: PhysicalProcess | Processes or Events involving physical objects and actions |
| Class: Organism | Organism |
| Class: Virus | Viruses |
| Class: CellularOrganism | cellular organisms |
| MetaClass: ECClass | Instances are Classes which form the standard classification scheme for enzymatic reactions |
| MetaClass: ProteinFamilyLevel | Instances are Classes related to gene expression and protein function at the level of families of protein function and structure. |
| MetaClass: LocusLevel | Instances are Classes related to gene expression and protein function at the species-specific Chromosome Location level. More general than SpliceVariantLevel, more specific than ProteinFamilyLevel |
| MetaClass: SpliceVariantLevel | Instances are Classes related to gene expression and protein function at the level of specific splice variants |
| X keggMapID Y | the object X is referenced on the map with the ID Y in the KEGG database |
| X ecNumber Y | enzymes or enzymatic reactions of type X are assigned the designation Y by the Enzyme Commission database |
| X genbankAC Y | the Genbank Database refers X to by the accession number Y |
| X genbankID Y | X is referred to by the id Y by the Genbank Database" |
| X unigeneAC Y | X is referred to by the accession number Y in the UniGene Database unigeneAC term2InstanceOf StringLiteral Value |
| X locuslinkID Y | the ID Y in the LocusLink Database refers to X |
| X locuslinkName Y | X is referred to by the name Y in the LocusLink Database |
| X refseqID Y | the ID Y in the RefSeq Database refers to X |
| X pfamID Y | the ID Y in the PFAM Database refers to X |
| X omimID Y | X is referenced in an article with ID Y in the OMIM Database |
| X prositeID Y | the ID Y in the Prosite Database refers to X |
| X smartID Y | the ID Y in the Smart Database refers to X |
| X casID Y | chemical type X is referred to by the ID Y in the CAS Database |
| X keggCompoundID Y | chemical type X is referred to by the ID Y in the KEGG Database |
| X keggReactionDoc Y | reaction type X is documented by the string Y in the KEGG Database |

-continued

| | |
|---|---|
| X keggReactionID Y | reaction type X is referred to by the ID Y in the KEGG Database |
| X keggOrganismID Y | organism type X is referred to by the ID Y in the KEGG Database |
| transfacAC | Accession number in the Transfac database |
| transfacID | ID string in the Transfac database |
| pirID | ID string in the PIR database |
| pirAC | Accession number in the PIR database |
| swissProtID | ID string in the SwissProt database |
| swissProtAC | Accession number in the SwissProt database |
| pubmedID | ID string in the Entrez PubMed database |
| emblID | ID string in the EMBL database |
| transfacOrganismName | organism name used in Transfac database (only recorded when different from NCBI name) |
| X geneName Y | Gene X has the official name Y |
| X geneSymbol Y | Gene X has the official symbol Y |
| X aliasGeneSymbol Y | Gene X is also known by symbol Y |
| X goAnnotation Y | things of type X are annotated with the Gene Ontology (GO) Database term Y |
| Class: Interaction | General class of events or processes Chemicals and/or cellular components affect each other |
| Class: Reaction | Chemical Reactions |
| Class: EnzymaticReaction | Reactions catalyzed by Enzymes |
| Class: Binding | |
| Class: Unbinding | |
| Class: NucleicAcidBinding | |
| Class: DNA Binding | |
| Class: DNA-TranscriptionFactor Binding | Binding in which a transcription factor binds to a segment of DNA |
| | RNA Binding |
| Class: RNA-TranscriptionFactor Binding | Binding in which a transcription factor binds to a segment of RNA |
| Class: GeneExpression | |
| X catalyzedBy Y | reactions of type X are catalyzed by enzyme molecules of type Y |
| X reactant Y | reactions of type X consume chemicals of type Y |
| X product Y | reactions of type X produce chemicals of type Y |
| X cofactor Y | the chemical with the name Y binds to the enzyme as a necessary cofactor in reactions of type X. It should imply X reactant Y. |
| X effector Y | Interactions of type X are effected by Chemicals whose name is Y. |
| X inhibitingChemical Y | Interactions of type X are inhibited by Chemicals whose name is Y. |
| X chemicalFormula Y | chemical type X has the formula Y" |
| X hasProteinBindingDomain Y | proteins of type X have a ProteinDomain of type Y" |
| X expressesGene Y | X is a type of GeneExpression that expresses Gene Y |
| X geneProduct Y | indicates that Chemical Y is produced by GeneExpression of type X |
| X upregulatedBy Y | GeneExpressions of type X are upregulated by Things of type Y |
| X downregulatedBy Y | GeneExpressions of type X are downregulated by Things of type Y |
| X regulatedBy Y | GeneExpressions of type X are affected by Things of type Y |
| X translatesRNA Y | RNA of type Y is translated as part of GeneExpression of type X |
| X homologousGene Y | Gene X is homologous to Gene Y |
| X isTranscribedToRNA Y | there exists gene expression such that Gene X is transcribed to RNA Y |
| X isTranslatedToProtein Y | there exists gene expression such that RNA X is translated to Protein Y" |
| X transcriptionModulationSite Y | Y is a binding site that affects the transcription of Gene X |
| X cytogeneticPosition Y | Y is the location of gene X within its chromosome |
| X onChromosomeNumber Y | the number of the chromosome on which a gene is located. Only makes sense if the gene is species-specific |
| X syntheticallyLethalWith Y | either Gene X or Gene Y is sufficient for the organism to survive, but at least one is required. |
| X location Y | things of type Y may be found at, on, or in physical objects of type X |

| | -continued |
|---|---|
| X bindingInput Y | bindings of type X involve molecules or molecular complexes of type Y |
| X bindingOutput Z | bindings of type X produce complexes of type Z |
| Class: MolecularComplex subsetOf Chemical | |
| X complexComponent Y | complexes of type X include molecules or molecular complexes of type Y |
| X complexComponent Y N | complexes of type X include N molecules or molecular complexes of type Y |
| X phosphorylatedAt N | Polymers of type X are phosphorylated at position N |
| X acetylatedAt N | Polymers of type X are acetylated at position N |
| X ribosylatedAt N | Polymers of type X are ribosylated at position N |
| X cleavedAt N | Polymers of type X are the remainder after cleavage at position N |
| X glycosylatedAt N | Polymers of type X are glycosylated at position N |
| X methylatedAt N | Proteins of type X are methylated at position N |
| X lipidatedAt N | Proteins of type X are lipidated at position N |
| X fattyAcylatedAt N | Proteins of type X are fattyAcylated at position N |
| X metallationAt N | Proteins of type X are metallated at position N |
| X hydroxylatedAt N | Proteins of type X are hydroxylated at position N |
| X sulfatedAt N | Proteins of type X are sulfated at position N |
| Class: ProteinDegradation subsetOf EnzymaticReaction | |
| Class: ProteinDegradation subsetOf EnzymaticReaction | |
| Class: Modulation subsetOf Process | |
| Class: Activation subsetOf Modulation | |
| Class: Inhibition subsetOf Modulation | |
| Class: DirectActivation subsetOf Activation | |
| Class: DirectInhibition subsetOf Inhibition | |
| X activates Y | Things of type Y are activated by Activations of type X |
| X activator Y | Activations of type X are caused by Things of Type Y |
| X inhibits Y | Things of type Y are inhibited in Inhibitions of type X |
| X inhibitor Y | Inhibitions of type X are caused by Things of Type Y |
| X competesWith Y | Processes of type X compete with Processes of type Y |
| X requires Y | Processes of type X require the presence of objects or processes of type Y. |
| Translocation subsetOf Process | |
| X translocatedObject Y | Things of type Y change location in Translocations of type X |
| X fromLocation Y | In Translocations of type X, the objects that change location are initially at locations of type Y. |
| X toLocation Y | In Translocations of type X, the objects that change location move to locations of type Y. |
| X connectedLocation Y | In Translocations of type X, the objects that change location may start or end at locations of type Y. |
| Class: Dimer | |
| Class: Trimer | |
| Class: Tetramer | |
| Class: Dimerization | |
| Class: Trimerization | |
| Class: Tetramerization | |
| Class: Exposure to Ionizing Radiation | |
| Class: Centromere DNA | |
| Class: Single-Stranded DNA | |
| Class: Double-Stranded DNA | |
| Class: DNA Lesion | |
| Class: Double-Stranded DNA terminus | |
| Class: Single-Stranded DNA break | |
| Class: SecretedProtein | |

It will be understood that in addition to the material listed in the table, a variety of other classes, primarily used for book-keeping, or to provide a place for objects in a unified class structure may be used in an actual implementation. For example, a high-level term, such as "Thing" may be used as the root for all classes, metaclasses and relationships. Additionally, relationships such as "X documentation Y" may be used to represent system information, such as documentation, in a knowledge base made up of case frames.

As seen in FIG. 7G, case frames can be combined and interconnected to represent complex biological information, such as pathways. FIG. 7G shows a pathway that includes binding.

Figure 8:
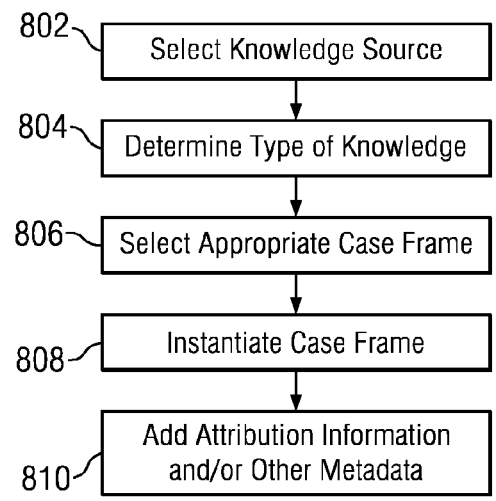
FIG. 8 is a flowchart illustrating an embodiment of a method for creating a case frame according to the present invention.

Referring now to FIG. 8, the process of creating a case frame is described. In step 802, the knowledge source is selected. In an exemplary embodiment, the knowledge for case frames can come from text, from a human, or from a database.

Once the knowledge source is identified, in step 804, the type of knowledge is determined. This is done by determining the type of entities being described (e.g. genes) and the types of relationships being imposed on the entities by the knowledge. For example, an entry for literature references of Genes represents a different type of knowledge than information about intra Gene activation and inhibition.

Next, at step 806, an appropriate case frame is chosen to represent the knowledge. Based on the type of knowledge to be represented, an appropriate set of case frames can be chosen from a library of generic case frames. In some instances, an appropriate case frame may not be available. When this occurs, it may be desirable to edit an existing case frame, or to add a new case frame.

When the case frames in the library are incomplete, or inadequate for representing the knowledge, it may be desirable to edit an existing case frame. For example, a case frame for representing a protein binding may not have in its template a field for entering the energy level of the binding. If this is the case, a new field may be added using a user interface. In some embodiments, an expert review may be required before a permanent change or addition is made to a case frame.

If a needed case frame does not exist, a new type of relation may be created and its attributes described in a new type of case frame. A user interface may be used to add a new type of case frame to the library of generic or empty case frames. In some embodiments, an expert review may be required before a new case frame is added to a library.

In step 808, the selected case frames are instantiated. Generally, instantiating a case frame involves filling in the blanks in the generic or empty template of the case frame. This is typically done through use of a user interface. Typically, a user reads each piece of knowledge from the original source, and fills in the fields in the Case Frame template to represent the knowledge. Once instantiated, the case frame is stored in a knowledge base for future use.

In step 810, metadata, such as attributions are added to the knowledge represented in a case frame. Each piece of knowledge (i.e., each line in the case frame) has an associated attribution. An attribution is a number or code that indicates when and where the data came from: the source, the person entering it, the date, time and experimental conditions from which the piece of knowledge was derived. Other metadata or context data (e.g. from which database the knowledge was derived, what type of information is represented by the knowledge, etc.) also may be added to the knowledge represented by a case frame.

Many of the steps described above may be performed by a user, through a user interface. In one embodiment, the user interface for entering knowledge is designed to be fool proof and enforces an ontology. The system is pre-loaded with an ontology of relevant biological terms and relations. Through a series of searches and pull-down menus, the user selects the entities he/she wants to relate (e.g. genes, proteins, metabolites), and then selects the relation (from the case frame library) and fills in the fields. Because the user can only relate terms that are already in the ontology, the user is kept from filling in unknown terms or incorrect spellings. If a new item or term is needed, then the new item or term may be entered into the ontology by an expert administrator of the system.

The ontology generally provides a kind of life science "markup", that adds meaning to life science information stored in the knowledge base, and facilitates the interconnection of pieces of information stored in the knowledge base. In accordance with an embodiment of the invention, the knowledge base provides a harmonization of life taxonomies, ontologies, and ways to make relationships.

In addition to permitting users to enter knowledge, knowledge may be extracted from databases. In many embodiments, the bulk of the knowledge in the knowledge base is loaded automatically. Generally, knowledge may be automatically loaded from structured databases and unstructured text sources. The databases are loaded using special purpose translation programs or software agents that translate the source format to a format compatible with the case frames. For example the source format may be a relational database or a XML file.

Text mining techniques are used to automatically extract knowledge from text documents. The extracted knowledge is then converted to case frames, and is loaded into the knowledge base. In some embodiments, known text mining tools, such as the products of ClearForest corporation, of New York, N.Y., the products of X-Mine Inc., of Brisbane, Calif., or text mining tools provided by Professor James Pustejovsky, of Brandeis University, of Waltham, Mass. may be used to extract relations between entities of interest.

As knowledge is added to the knowledge base through use of case frames, connections between the various pieces of knowledge may be formed. In some embodiments, these connections are implicit, and arise as the result of the same entity being used in multiple relationships. A knowledge base for use in the life sciences may contain well over a million pieces of knowledge, and millions of connections between those pieces of knowledge.

Figure 11:
FIG. 11 shows an example of a screen in which two terms used in a life science ontology are merged according to an embodiment of the invention.

FIGS. 9-11 show example screens of a user interface used in one embodiment of the invention for creating case frames. FIG. 9 shows a screen 850 of a user interface for searching and viewing the case frames associated with a particular chemical. In the example shown in the screen 850, a search area 852 is used to specify a search for case frames associated with pyruvate. The results of the search are shown in a case frame list area 854.

Generally, the search area 852 may be used to enter various queries on the knowledge base, permitting a user to browse through the all the knowledge associated with a particular entity, and all related entities.

In FIG. 10, a screen 900 is shown, in which a drop down menu 902 is used to permit a user to select a relationship type. An area 904 allows the user to determine terms in the ontology that may legally be entered in various parts of the relationship selected in the drop down menu 902.

FIG. 11 shows a screen 1000 in which two terms in the ontology are being merged. Using a merge area 1002, a user may specify that two terms in the ontology have the same meaning, enter a new name for the two merged terms, and view all case frames using either or both of the terms.

In addition to a user interface similar to the examples shown in FIGS. 9-11, other tools may be used to create case frames. For example, known tools for creating graph representations of knowledge, such as Knowledge Editor, available from the Genomic Sciences Center of RIKEN (the institute of physical and chemical research) Yokohama Institute, in Japan, can be used to create case frames. The output from such tools may be processed using data manipulation software, such as Perl, to generate case frames based on the output from such tools.

Once the knowledge base of instantiated case frames is constructed, a variety of algorithms may be applied to reason using the knowledge. Such reasoning algorithms are typically research and purpose specific. For example, reasoning algorithms may include algorithms that find the shortest path between two entities, find the shortest path between two entities that goes through a third entity, find a molecule that controls numerous other molecules (or is upstream of a process of interest), determine which enzymes and metabolites will be impacted if an enzyme is inhibited, determine what will happen if a gene is knocked out, or determine the results if multiple entities are knocked out.

Figure 13:
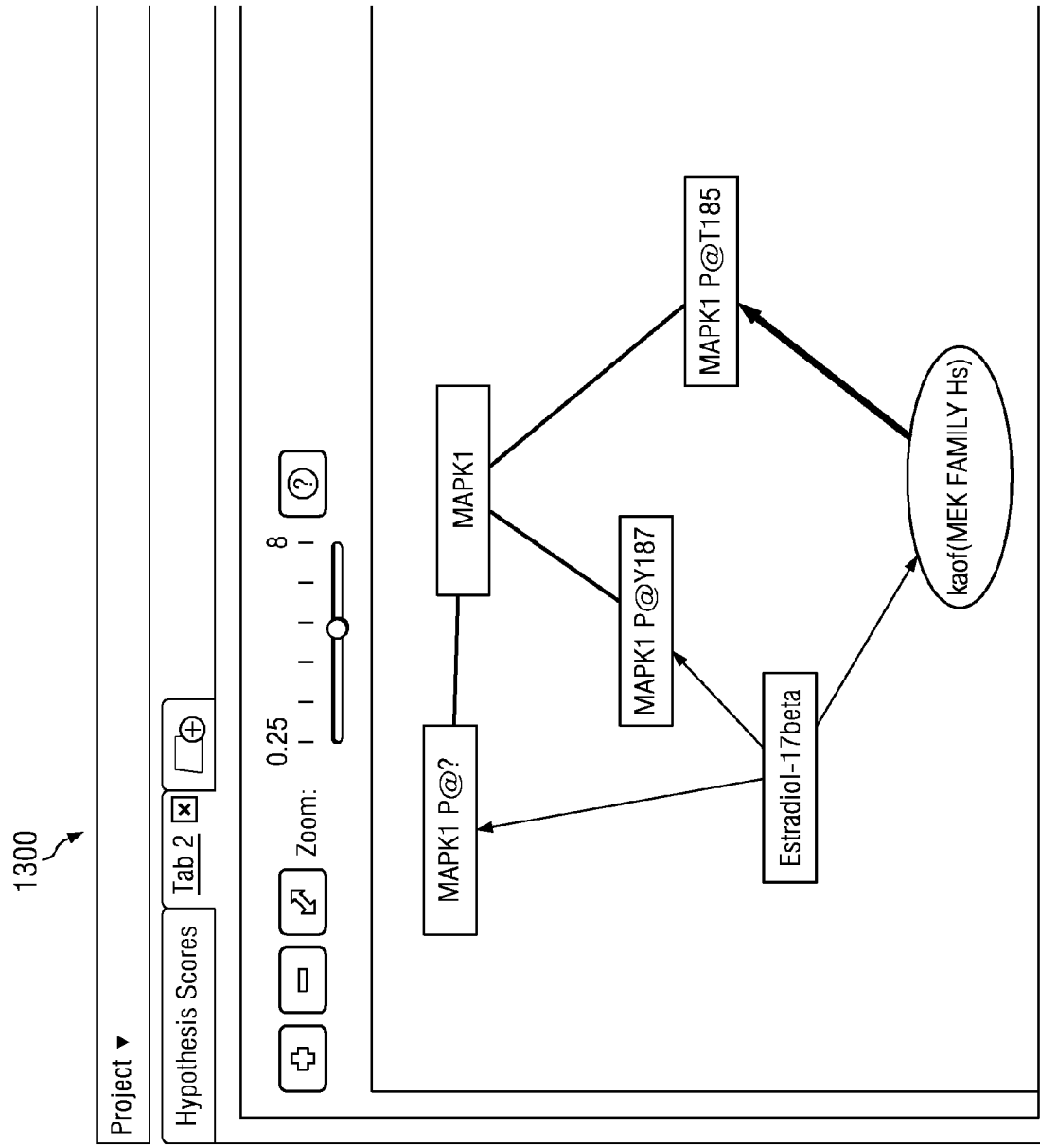
FIG. 13 shows a screen that displays a graphical representation of paths according to an embodiment of the invention.

As discussed above with reference to FIG. 2, the knowledge base may be viewed as a graph, containing nodes which represent entities, and edges which represent relations between the entities. By using algorithms that traverse, manipulate, or search this graph, the system is able to effectively reason about the knowledge contained in the knowledge base. One application of such algorithms is shown above, in FIG. 9, in which a user is able to query the knowledge base, and browse through knowledge associated with an entity and all related entities. FIGS. 12 and 13 show another example application of such algorithms, in which the system reasons about pathways.

FIG. 12 shows a screen 1200, in which a graph theory-based search algorithm is used to look for all the pathways between two metabolites. In a selection area 1202, the user selects the two metabolites—Zymosterol and Ergosterol, in this example. In a pathway results area 1204, the system displays a list of possible pathways, based on a graph theory-based search of the knowledge base.

Once these pathways have been found in the graph, a graphical representation of the pathways may be generated. In FIG. 13, screen 1300 shows such a graphical representation of the pathways between two metabolites. This graphical representation may be automatically generated by the system, an may be used by scientists to understand the pathways and the mechanism of action of any perturbations being made to the system and the resulting experimental results.

Figure 14:
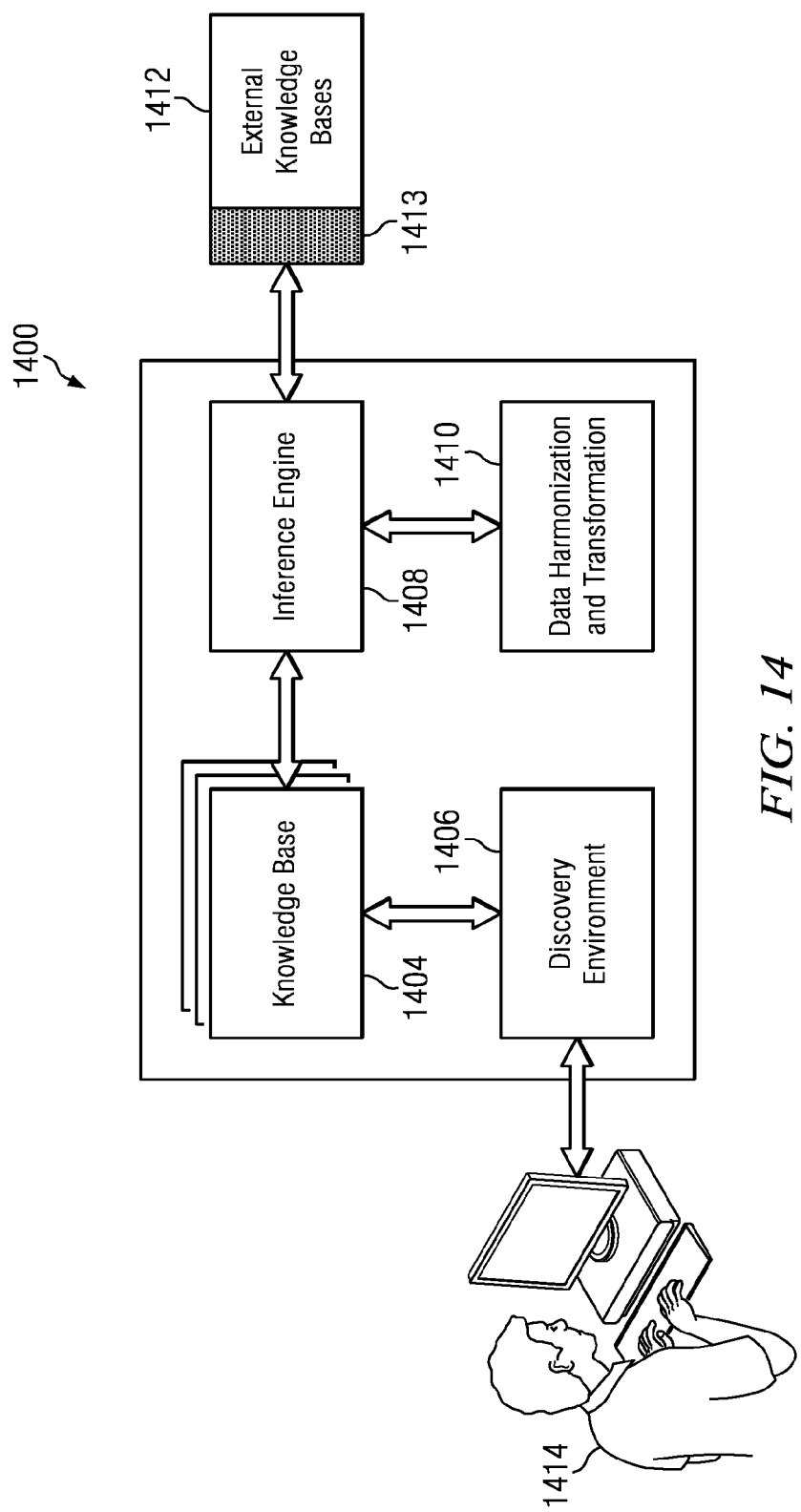
FIG. 14 is a block diagram showing the structure of a life science discovery system according to an embodiment of the present invention.

Referring now to FIG. 14, an overview of one embodiment of a system according to the invention that combines these knowledge acquisition and manipulation capabilities is described. The system 1400 includes one or more knowledge bases 1404, a discovery environment 1406, an inference engine 1408, and a data harmonization and transformation module 1410.

The knowledge bases 1404 contain life science knowledge that is created, stored, and organized as described hereinabove. In some embodiments, the knowledge bases may be multi-tiered. A user 1414 may have a personal knowledge base (also referred to as a "sandbox"), which incorporates specialized pieces of knowledge that the user has entered. The user 1414 may also access a group knowledge base, a departmental knowledge base, a company knowledge base, etc.

Each level in this multi-tiered access scheme may include access to other levels. Thus, when accessing a personal knowledge base, the user 1414 may access knowledge (and implicit connections between knowledge items) in the personal knowledge base, combined with the knowledge in the group knowledge base, the departmental knowledge base, and so on.

In addition to storing knowledge, the knowledge base 1404 may store agents definitions, the ontology, and other data that is used by the system 1400.

The discovery environment 1406 provides a user interface through which the user 1414 may access knowledge in the knowledge bases 1404, and other knowledge bases accessible through the system 1400. Additionally, the discovery environment 1406 may include discovery tools, that may be used to automatically reason about information contained in the knowledge bases 1404. For example, a tool for automatically discovering and displaying pathways, such as is shown above with reference to FIGS. 13 and 14 may be a part of the discovery environment 1406. Alternatively, some tools for reasoning about the knowledge stored in the knowledge bases 1404 may be included in the inference engine 1408.

The inference engine 1408 manages the life sciences ontology that is used, for example, when new entries are added to the knowledge bases 1404. Additionally the inference engine 1408 manages knowledge agents, that automatically create connections or relationships between entries in the knowledge bases 1404, based on rules.

The data harmonization and transformation module 1410 manages data integration agents, which keep the knowledge bases 1404 up to date from various legacy and public sources. Such data integration agents may periodically access various sources of life sciences data, and translate such data into a form that may be integrated into the knowledge bases 1404. Integration of such data into the knowledge bases 1404 may involve automatically generating appropriate relations within the data that is being integrated, and between the data that is being integrated and other data and entities in the knowledge bases 1404. This task may be handled by the knowledge agents of the inference engine 1408.

In addition to providing access to knowledge stored in the knowledge bases 1404, the system 1400 may provide access to various external knowledge bases 1412. The external knowledge bases 1412 may include knowledge bases assembled by universities, other researchers, companies, and so on. Additionally, such external knowledge bases may include agent definitions, ontologies, and other data that may be used by the system 400.

Access to any particular external knowledge base may be controlled through a managed account interface 1413. The managed account interface 1413 may be used to restrict access to various external knowledge bases, or to permit only selected portions of such knowledge bases to be accessed externally. For example, the managed account interface 1413 may be used to permit external access to a knowledge base only to a set of subscribers. Additionally, managed account interface 1413 may manage a directory, log files log, and update history information.

In some embodiments, Discovery Environment 1406 may include a managed account interface (not shown) similar to managed account interface 1413. Such an interface can be used to identify users, restrict access, keep logs, manage updates, manage a directory, and other similar administrative tasks.

As discussed above, in some embodiments, the knowledge base may be multi-tiered, and may include access restrictions. As shown in FIG. 15, portions of the knowledge base may be proprietary. These proprietary portions may only be accessed by the owner of the proprietary information. Information in the proprietary sections of the knowledge base may be linked to other information within the knowledge base.

Knowledge base 1500 includes a public knowledge base 1502, a subscriber knowledge base 1504, and proprietary knowledge bases 1506 and 1508. The public knowledge base 1502 contains life science information that may be accessed by members of the public 1510. Subscribers 1512 may access everything in the public knowledge base 1502, as well as the information in the subscriber knowledge base 1504. Information in the subscriber knowledge base 1504 may have greater commercial value than the information in the public knowledge base 1502.

The proprietary knowledge base 1506 may add information to the knowledge base 1500 that is owned by a particular individual or company. A user 1514 who has legitimate access to the proprietary knowledge base 1506 is able to access all of the information in the proprietary knowledge base 1506, the subscriber knowledge base 1504, and the public knowledge base 1502. All of this information will appear to the user 1514 to be interrelated, to form a seamless whole. The information stored in the proprietary knowledge base 1506, and the relationships between that information and information stored in other portions of knowledge base 1500 will only be visible to users, such as the user 1514, who have access to the proprietary knowledge base 1506.

Similarly, the proprietary knowledge base 1508 may only be accessed by users, such as a user 1516, who have legitimate access to the proprietary knowledge base 1508. The user 1516 does not have access to the proprietary knowledge base 1506, and is unable to access any of the information or relations with information in the proprietary knowledge base 1506. The user 1514 does not have access to the proprietary knowledge base 1508, and is therefore unable to access to any of the information or relations with information in the proprietary knowledge base 1508. Similarly, subscribers 1512, and the public 1510 are unable to access information or relations to information in either of the proprietary knowledge bases 1506 or 1508. Access to information in these proprietary knowledge bases is blocked by security measures 1518.

In accordance with the invention, case frames relating life sciences information may be used to represent all aspects of the functioning and structure of biological systems and their components. Thus, while the majority of this specification speaks in terms of biochemical data at the physiologic level, case frames may be used to represent interactions at the levels of ions and atoms, nucleic acid, protein, and metabolite biochemistry, organelles, subcellular compartments, cells, tissue compartments, tissues, organs, organ systems, individuals, populations, diet, diseased states, clinical trials, epidemiology, predator prey interactions, and parasite-host interactions.

Examples of biological systems in the human context include, but are not limited to, the integument, skeletal, muscular, nervous, endocrine, cardiovascular, immune, circulatory, respiratory, digestive, urinary, and reproductive systems. In one particular example, case frames could be used to represent the functioning and structure of skeletal muscle fibers in the muscular system. In another example, case frames could be used to represent the functioning of neural control of muscle fiber contraction in the skeletal system. In further examples, case frames could be used to represent the functioning and structure of pathways for visceral motor output or the functioning of synaptic communication in neural tissue in the nervous system. In other examples, case frames could be used to represent the functioning and structure of cardiac cycle and control of heart rate in the cardiovascular system. In yet other examples, case frames could be used to represent the functioning and structure of lymphocytes and immune response in the lymphatic system.

Examples of cells modeled using case frame technology include, but are not limited to, epithelial cells, nerve cells, blood cells, connective tissue cells, smooth muscle cells, skeletal muscle cells, fat cells, ovum cells, sperm cells, and stem cells. Examples of cell functions include, but are not limited to, cell division, cell regulation, control of cellular activity by the nucleus, and cell-to-cell signaling. Case frames may be used to represent the functioning and structure of cellular components. Examples of cellular components include, but are not limited to, the cytoplasm, cytoskeleton, ribosomes, mitochondria, nucleus, endoplasmic reticulum (ER), Golgi apparatus, and lysosomes.

In a further embodiment, case frames may be used to represent the structure, function and synthesis of proteins. In addition, case frames could be used to represent components of proteins, including, but not limited to, amino acid sequence, secondary and tertiary structure, conformation data. Furthermore, case frames could be used to represent molecules associated with proteins, including, but not limited to, enzymes.

In another embodiment, case frames from life sciences information are used to represent the structure, function and synthesis of nucleic acids. Nucleic acids are not limited to any particular type of nucleic acid and include, but are not limited to, total genome DNA, cDNA RNA, mRNA, tRNA, and rRNA. In another embodiment, case frames from life sciences information are used to represent the structure and function of DNA replication, DNA repair, and DNA recombination. In a further embodiment of the invention, case frames identify, for example, a single nucleotide polymorphism (SNP), a splice variant, microRNA, double-stranded RNA (dsRNA), small interfering RNA (also known as short interfering RNA or siRNA), RNA interference (RNAi), a chromosome, a chromosomal modification or a silenced gene.

In yet another embodiment, case frames from life sciences information are used to represent cancer pathways, including, but not limited to, the functioning of oncogenes and tumor suppressor genes. For example, gene expression of the human p53 tumor suppressor gene is shown as multiple case frames in FIG. 7C. In another embodiment of the invention, case frames may be used to represent the pathways for various types of cancer, including, but not limited to, cancers of the blood, stomach, lung, liver, pancreas, prostate, kidney, testes, bladder, uterus, colon and rectum.

In a further another embodiment, case frames from life sciences information are used to represent the pathways for various types of diseases, including, but not limited to, the functioning of molecular mechanisms underlying diseases. Examples of diseases include, but are not limited to, cardiovascular, coronary, pulmonary, respiratory, hematologic, neurological, psychiatric, neuropsychological, neuromuscular, musculoskeletal, ophthalmological, gastrointestinal, genitourinary, endocrinal, dermatologic, inflammatory, metabolic, pathogenic, and infectious diseases.

In another embodiment of the invention, case frames include patient data. Patient data may include data of phenotypic or genotypic nature. For example, patient data could include, but is not limited to, LDL level, cholesterol level, and white blood cell level. In other examples, patient data includes, but is not limited to, diagnosis of congestive heart failure (CHF) and diagnosis of end stage renal disease (ESRD). In a further example, genotypic patient data includes, but is not limited to, detection of single nucleotide polymorphisms (SNPs).

In one embodiment of the invention, case frames from life sciences information identify a product relationship. Examples of such relationships include, but are not limited to, the following: drug X inhibits a specific function of molecule Y; chemical X acts as a drug; chemical X is in a published patent; chemical X is used to treat disease Y; chemical X inhibits the activity of entity Y; and chemical X activates the ABC activity of entity Y.

In yet another embodiment, case frames can identify experiments that are linked to characteristics and parameters. For example, a case frame could identify an experiment that links a result file or a protocol file from the experiment. In another example, a case frame could identify that an experiment was conducted by a particular person or facility. In a further example, a case frame could identify that an experiment has one or more sub-experiments or mini-experiments. In another embodiment of the invention, case frames could identify and relate data from an animal experiment or tissue type used in an experiment.

In another embodiment, case frames may be used to represent the functioning and structure of infectious agents. Examples of such infectious agents include, but are not limited to, viruses, bacteria, yeasts fungi, or other microorganisms such as parasites. In yet another embodiment, case frames identify a pathogen such as a virus, bacteria, fungus or prion, with relationship connectors representing implications in specific diseases and other characteristics. In other embodiments of the invention, case frames identify that a particular measurable entity is a biomarker for a disease state, drug efficacy, or patient stratification, identify the relationship between model organisms, tissues or other biological models of disease, and the relevant disease(s), or an epidemic and its characteristics.

In another embodiment, case frames identify a disease that links to characteristics, biomarkers, mechanisms, or genes. For example, a case frame could link breast cancer with the BRCA-1 gene. As another example, a case frame could link chronic lymphocytic leukemia (CLL) with the Bcl2 gene. In a further embodiment, case frames identify a population with relationship connectors representing characteristics. For example, a case frame could identify a certain population as having a high incidence of sickle cell anemia or breast cancer. In another embodiment of the invention, case frames identify a xenograft model. In a further embodiment of the invention, case frames identify a cell line and its characteristics. For example, a case frame could identify a cell line having a mutant k-Ras gene and a normal p53 gene.

Although case frames of the invention have been described with reference to specific embodiments, it should be understood by those skilled in the art that various changes in form and detail may be made therein without departing from the spirit and scope of the invention. In accordance with the invention, case frames may be used to represent any life-science information.

In some embodiments, the functionality of the systems and methods described above may be implemented as software on a general purpose computer. In such an embodiment, the program may be written in any one of a number of high-level languages, such as FORTRAN, PASCAL, C, C++, LISP, JAVA, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, a "computer-readable medium" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A computer system for storing life science information in a database, the computer system comprising:
    a processor;
    an electronic database storage module for storing in the database a library of machine-readable symbolic representations into which life science knowledge is adapted to be encoded according to a life sciences ontology, each machine-readable symbolic representation comprising:
        at least two unspecified object identifiers;
        a relationship connector, wherein the relationship connector relates two of the at least two object identifiers to each other based on a casual relationship between the object identifiers; and
        constraint information that defines which connections among the object identifiers are permitted so that life sciences knowledge encoded into the machine-readable symbolic representation is semantically rigorous and based on the life sciences ontology; and
    a graphical user interface for managing addition of new life sciences data to a database, the graphical user interface comprising:
        a display screen that receives an input selecting one of the machine-readable symbolic representations as a template to represent the new data based at least in part on the life science ontology;
        the graphical user interface restricting input of any data element that does not conform to the constraint information associated with the selected machine-readable symbolic representation such that the semantically rigorous relationships for the life sciences ontology are maintained;
        the graphical user interface receiving input of at least one data element that conforms to the constraint information to instantiate the machine-readable symbolic representation.

2. The computer system of claim 1, wherein a set of machine-readable symbolic representations define one of: a biological function, and a chemical reaction.

3. The data processing computer system of claim 2, wherein the biological function comprises one of: transport, and digestion of a biomolecule.

4. The computer system of claim 1, wherein at least one of the at least two object identifiers identifies one of: a biomolecule, and a biological function.

5. The computer system of claim 1, wherein at least one of the at least two object identifiers identifies a relationship connector.

6. The computer system of claim 1, wherein at least one of the at least two object identifiers identifies an identity relationship.

7. The computer system of claim 1, wherein the relationship connector represents one of: a product relationship, a substrate relationship, and an enzymatic relationship.

8. The computer system of claim 1 wherein the graphical user interface permits a user to query the database based on the relationship connector.

9. The computer system of claim 1 further comprising an access manager configured to restrict access to one or more portions of the electronic database.

10. The computer system of claim 1 further comprising an inference engine executed by the processor.

11. The computer system of claim 10 wherein the inference engine provides modifications to at least one machine-readable symbolic representation, wherein the modifications comprise one or more of the addition of new fields, the addition of new relationships, and the addition of metadata.

12. The computer system of claim 10 wherein the metadata comprises one or more sources of the new data, a date the new data was received, a time the new data was received, and one or more experimental conditions under which the new data was created.

13. The computer system of claim 1 further comprising a harmonization and transfer module executed by the processor to interface with multiple disparate sources of life science data.

14. The computer system of claim 13 wherein the harmonization and transfer module further translates given data into a data format compatible with at least one machine-readable symbolic representation.

15. The computer system of claim 1 wherein the graphical user interface displays pathways among the plurality of machine-readable symbolic representations, the pathways representing causal relationships among the machine-readable symbolic representations.

16. The computer system of claim 1 further comprising a managed account interface executed by the processor to attribute access restrictions to one or more machine-readable symbolic representations in the database, the access restrictions comprising one of: public access rights, subscription-based access rights, and proprietary access rights.

17. The computer system as described in claim 1 wherein the database comprises machine-readable symbolic representations representing enzyme reactions, binding interactions, modifications of polymers, protein phosphorylation reactions, gene expressions, acetylation, peptide-bond cleavage, glycosylayion, lipidation, fatty-acylation, methylation, metallation, cross-linking, hydroxylation, sulfation, ADP-ribosylation, translocation and transcriptional activations.

18. The computer system of claim 1 wherein at least one machine-readable symbolic representation represents a protein phosphorylation reaction comprising a reactant, a product, and a catalyst.

19. The computer system of claim 1 wherein at least one machine-readable symbolic representation represents a gene expression comprising a gene and a gene product.

20. The computer system of claim 1 wherein at least one machine-readable symbolic representation represents a transcriptional activation comprising a gene expression, an activation, and a transcriptional activator.

21. The computer system as described in claim 1 wherein a machine-readable symbolic representation is XML or pseudocode.

22. The computer system as described in claim 1 wherein at least first and second machine-readable symbolic representations in the database comprise a knowledge base of semantically-rigorous life sciences representations against which one of more reasoning algorithms are applied.

23. The computer system as described in claim 22 wherein applying a reasoning algorithm generates one or more pathways associated with a query to the knowledge base.

24. The computer system as described in claim 23 wherein the one or more pathways are displayed in the graphical user interface.

25. The computer system as described in claim 1 wherein the graphical user interface receives attribution information identifying a source of the new life sciences data.

* * * * *